United States Patent
Riether et al.

(10) Patent No.: US 10,710,984 B2
(45) Date of Patent: *Jul. 14, 2020

(54) N-[(PYRIMIDINYLAMINO)PROPANYL]-AND N-[(PYRIDINYLAMINO)-PROPANYL]ARYL-CARBOXAMIDES

(71) Applicant: Boehringer Ingelheim International GmbH, Ingelheim am Rhein (DE)

(72) Inventors: Doris Riether, Biberach an der Riss (DE); Marco Ferrara, Sam Donato Milanese (IT); Niklas Heine, Biberach an der Riss (DE); Uta Lessel, Maselheim (DE); Janet Rachel Nicholson, Oberhoefen (DE); Anton Pekcec, Munich (DE); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/090,667

(22) PCT Filed: Apr. 7, 2017

(86) PCT No.: PCT/EP2017/058320
§ 371 (c)(1),
(2) Date: Oct. 2, 2018

(87) PCT Pub. No.: WO2017/178343
PCT Pub. Date: Oct. 19, 2017

(65) Prior Publication Data
US 2019/0112297 A1    Apr. 18, 2019

(30) Foreign Application Priority Data
Apr. 15, 2016    (EP) .................................... 16165541

(51) Int. Cl.
| C07D 403/12 | (2006.01) |
| C07D 401/14 | (2006.01) |
| C07D 401/12 | (2006.01) |
| C07D 417/12 | (2006.01) |
| A61K 51/00  | (2006.01) |

(52) U.S. Cl.
CPC ............ *C07D 403/12* (2013.01); *A61K 51/00* (2013.01); *C07D 401/12* (2013.01); *C07D 401/14* (2013.01); *C07D 417/12* (2013.01)

(58) Field of Classification Search
CPC combination set(s) only.
See application file for complete search history.

(56) References Cited

U.S. PATENT DOCUMENTS

| 7,468,367 | B2 * | 12/2008 | Coulton | C07D 403/12 |
|           |      |         |         | 514/249 |
| 9,884,854 | B2 * | 2/2018  | Riether | C07D 401/12 |
| 2015/0166523 | A1 | 6/2015 | Araki et al. | |

FOREIGN PATENT DOCUMENTS

| EP | 2862855 A1 | 4/2015 |
| WO | 03051872 A1 | 6/2003 |
| WO | 2009011775 A1 | 1/2009 |
| WO | 2016034882 A1 | 3/2016 |
| WO | WO 2016/034882 * | 3/2016 |
| WO | 2017178338 A1 | 10/2017 |
| WO | 2017178340 A1 | 10/2017 |
| WO | 2017178343 A1 | 10/2017 |
| WO | 2017178344 A1 | 10/2017 |

OTHER PUBLICATIONS

Scammell (Annu Rev Pharmacol Toxicol. Feb. 10, 2011; 51:243-266).*
Piccoli et al. (Neuropsychopharmacology (2012) 37, 1999-2011).*
Blouin et al. Nat. Connnnun. 2013; 4: 1547.*
International Search Report and Written Opinion for PCT/EP2017/058320 dated May 24, 2017.
International Search Report for PCT/EP2017/058312 dated May 24, 2017.
Written Search Report for PCT/EP2017/058312 dated May 4, 2017.
Suzuki, Discovery and invitro and in vivo profiles of N-ethyl-N-[2-[3-(5-fluoro-2-pyridinyl-)-1H-pyrazol-1-yl-ethyl]-2-(2H-1,2,3-triazol-2-yl)-benzamide asa novel class of dual orexin receptor antagonist, Bioorganic and Medicinal Chemistry, 2014.
International Search Report for PCT/EP2017/058314, dated May 19, 2017.
Written Opinion of the Internation Search Authority for PCT/EP2017/058314 dated May 19, 2017.
International Search Report for PCT/EP2017/058315 dated May 9, 2017.

\* cited by examiner

*Primary Examiner* — Valerie Rodriguez-Garcia
(74) *Attorney, Agent, or Firm* — Robert J. Kajubi

(57) ABSTRACT

The present invention relates to novel N-[(Pyrimidinylamino)propanyl]- and N-[(Pyridinylamino)propanyl] arylcarboxamide derivatives, processes for their preparation, pharmaceutical compositions containing them and their use in therapy, particularly in the treatment or prevention of conditions having an association with the orexin sub-type 1 receptor.

8 Claims, No Drawings

N-[(PYRIMIDINYLAMINO)PROPANYL]-AND N-[(PYRIDINYLAMINO)-PROPANYL]ARYL-CARBOXAMIDES

FIELD OF THE INVENTION

The present invention relates to novel N-[(Pyrimidinylamino)propanyl]- and N-[(Pyridinylamino)-propanyl] arylcarboxamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more).

Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8): e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders, such as borderline personality disorder, eating disorders such as binge eating disorder or attention deficit hyperactivity disorder. Therefore, it is desirable to provide an OX1R selective antagonist for the treatment of impulse control deficits.

Neuroimaging with Positron Emission Tomography (PET) ligands is a non-invasive clinical methodology that is frequently used to quantify the concentration of drugs reaching the pharmacological target, as it provides a direct measure of Receptor Occupancy (RO). In addition, PET ligands can be used to assess disease stage and progression as well as for patient stratification.

A PET ligand can be used in RO studies preclinically and clinically in order to support dose finding and generate a brain receptor occupancy plasma concentration relationship for clinical development. PET ligands are labelled with short-lived positron emitting radionuclides such as $^{11}$C or $^{18}$F. Diverse reagents are available for the introduction of positron-emitting radionuclides and are described for example by P. W. Miller et al. in Angewandte Chemie (International Ed.) 2008, 47, 8998-9033.

A biomathematical modeling approach (Guo et al, The Journal of Nuclear Medicine 2009, 50, 10 1715-1723) has the potential to predict the in vivo performance of compounds based on in silico and in vitro data and aid in the development of molecular imaging probes.

Physicochemical properties as described by L. Zhang et al. (J. Med. Chem. 2013, 56, 4568-4579) can be used to prioritize and accelerate the identification of PET ligands. Compounds suitable for OX1R PET ligand development need to be highly potent at OX1R and at least 100 fold selective over OX2R to ensure specific binding to the OX1R. The log P should be <4 in order to ensure sufficient unbound concentration in the brain. Further in vitro parameters to predict brain exposure is efflux assessed by MDCK efflux measurements. The clearance of a PET ligand should be high, therefore metabolic stability in human liver microsomes should be low.

Orexin receptor antagonists of various structural classes are reviewed in Roecker et al. (J. Med. Chem. 2015, 59, 504-530). WO03/051872, WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-[(Pyrimidinylamino)propanyl]- and N-[(Pyridinylamino)-propanyl] arylcarboxamide derivatives that unexpectedly are highly potent OX1R antagonists (assay A) further characterized by
1) high selectivity over the OX2 receptor (assay B),
2) no or low MDCK efflux (assay C), and
3) log P<4 (assay D).

Compounds of the present invention are potent OX1R antagonists.

Compounds of the present invention are though encompassed by formula I of WO03/051872, differ structurally from those explicitly disclosed therein in that they contain a central N-ethyl-(propan-2-yl)amino moiety in place of the N-methyl-ethylamino, NH-ethylamino, or NH-(propan-2-yl)amino moiety. These structural differences unexpectedly result in higher potency and higher selectivity over the OX2R Compounds of the present invention differ structurally from those disclosed in WO2013/187466 in that they contain a (5-trifluoromethyl-pyrimidin-2-yl)-amino or (5-trifluoromethyl-pyridin-2-yl)-amino moiety in place of a Het1-Het2 moiety in which Het2 is phenyl or pyridyl. These structural differences unexpectedly result in a higher potency and selectivity.

Compounds of the present invention differ structurally from Examples 1, 14, 39, 42, 71, 73, 84 and 91 in WO2016/034882 (closest prior art) in that they contain a central N-ethyl-(propan-2-yl)amino moiety in place of the N-ethyl-[butan-2-yl]amino, N-methyl-[prop-2-yl]amino or N-methyl-[butan-2-yl]amino moiety. These structural differences unexpectedly result in a higher potency at OX1R and in most cases higher OX1R selectivity.

Due to their higher potency at the OX1R, in combination with high OX1R selectivity, their log P and MDCK efflux properties, compounds of the present invention are expected to be more suitable as ligands for PET radiolabelling as compared to the closest prior art compounds.

General Definitions

Terms not specifically defined herein should be given the meanings that would be given to them by one skilled in the art in light of the disclosure and the context.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts,) also comprise a part of the invention.

BIOLOGICAL ASSAYS

Abbreviations

IP1 D-myo-inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:

A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 μL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM, and/or 50 nM for selected compounds) dissolved in assay buffer is added to the assay plate. The assay plate is incubated for 60 minutes at 37° C. Then 5 μL per well of Anti-IP1-Cryptate Tb solution and 5 μL per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/(2+(A/EC_{50})^n)^{1/n}-1)$ (with A=concentration agonist, $EC_{50}$=$EC_{50}$ agonist, n=Hill slope agonist) (see P. Leff, I. G. Dougall, Trends Pharmacol. Sci. 1993, 14(4), 110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 5000 cells/25 μL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay. On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM) dissolved in assay buffer is added to the assay plate. The assay plate is incubated for 60 minutes at 37° C. Then 5 μL per well of Anti-IP1-Cryptate Tb solution and 5 μL per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

C. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4$—$H_2O$, 15 mM HEPES, 20 mM glucose, 0.25% BSA, pH 7.4) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by H PLC-MS/MS or scintillation counting. Sampled receiver volumes are replaced with fresh receiver solution.

D. Assessment of Log P

The assay was performed following the description by S. F. Donovan and M. C. Pescatore in J. Chromatogr. A 952 (2002) 47-61.

Biological Data

Comparison of Assays A and B with the Assays Described in WO03/051872

TABLE 1

In vitro potencies of compounds of WO03/051872 as reported therein versus as determined in the Assays A and B (described above)

Structure of Example 6 in WO03/051872

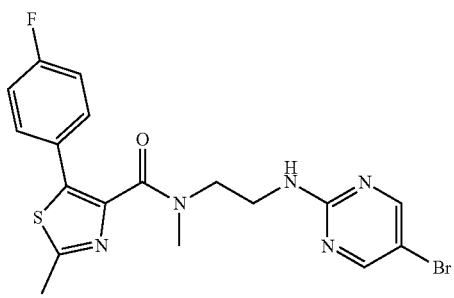 [SMILES: Cc1nc(C(=O)N(C)CCNc2ncc(Br)cn2)c(-c2ccc(F)cc2)s1]

| Data as described in WO03/051872 (page 16-18) | | |
|---|---|---|
| OX1R pKb = 6.4 to 7.4 corresponds to Kb = 400 to 40 nM | OX2R pKb < 6.6 to 7.4 corresponds to Kb > 250 to 40 nM | OX2R Kb/ OX1R Kb = not described |
| Data as determined in Assays A and B (0.5 nM Orexin A concentration) | | |
| Assay A: OX1R Kb = 30 nM | Assay B: OX2R Kb = 101 nM | OX2R Kb/ OX1R Kb = 3.4 |

Comparison of Assays A and B with the Assays Described in WO2013/187466

Assays described in WO2013/187466 differ from assays A and B in:

The technology and readout: fluorescence measurement of intracellular $Ca^{2+}$ changes (WO2013/187466) instead of luminescence measurement of IP1 (assays A and B)

Ox1R and Ox2R overexpressing cell lines used for the assays described in WO2013/187466 are of different origin as cell lines used for assays A and B Use of modified orexin A (2 amino acids substituted) as agonist instead of orexin A Agonist concentration of 300 pM used for the OX1R assay and 3 nM for the OX2R assay (EC75 vs. EC100; according to Okumura T. et al., Biochemical and Biophysical Research Communications, 2001) (WO2013/187466). $IC_{50}$ values that have been reported are dependent on the agonist concentration. Selectivity ratios calculated from these $IC_{50}$ values cannot be compared with the selectivity ratios calculated from the agonist concentration independent Kb values obtained from assay A and B.

Due to these differences between the assays, a direct comparison has to be established. Therefore, examples 69, 70 (the most selective ones) and 5 (one of the most potent ones) described in WO2013/187466 are tested in assays A and B so as to be directly compared with compounds of the present invention (see Table 2).

TABLE 2
In vitro potencies of compounds of WO2013/187466 as reported therein versus as determined in the Assays A and B (described above)
| Structure Example # in WO2013/187466 | As described in WO2013/187466 | | | As determined in Assays A and B | | |
|---|---|---|---|---|---|---|
| | OX1R IC$_{50}$ [nM] | OX2R IC$_{50}$ [nM] | OX2R IC$_{50}$/ OX1R IC$_{50}$ | OX1R Kb [nM] (Orexin A concentration used) | OX2R Kb [nM] (0.5 nM Orexin A concentration) | OX2R Kb/ OX1R Kb |
| 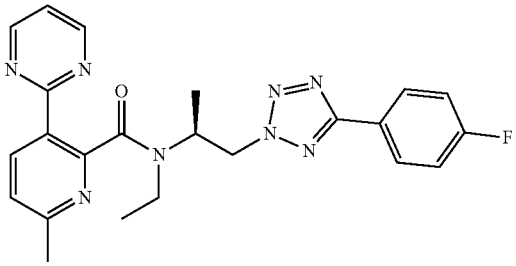 Example 69 | 1.6 | 1896 | 1185 | 2.25 (0.5 nM) | 98 | 43 |
| 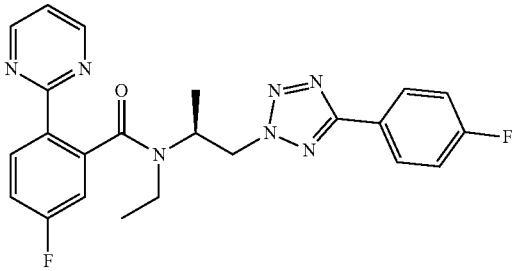 Example 70 | 1.1 | 452 | 411 | 1.10 (0.5 nM) 0.72 (50 nM) | 29 | 26 40 |
| 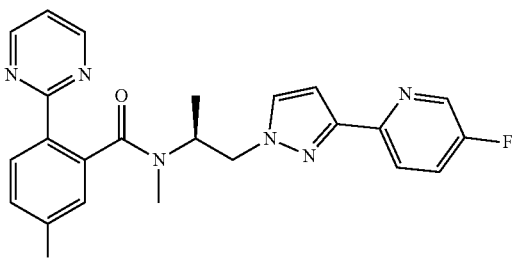 Example 5 | 0.5 | 76 | 152 | 1.78 (0.5 nM) 0.94 (50 nM) | 28 | 16 30 |

TABLE 3

In vitro potencies of the structurally closest prior art compounds (Example 70, 71 and 73) in WO2016/034882 as reported therein:

| Structure Example # in WO2016/034882 | As described in WO2016/034882 (Table 1 (Method 1), Table 2 (Method A), Table 3 (Method B), page177-180) | | |
|---|---|---|---|
| | OX1R | OX2R | OX2R $IC_{50}$/ OX1R $IC_{50}$ |
| Example 1 | Table 1: $pIC_{50}$ = 7.7 corresponds to $IC_{50}$ = 20 nM Table 2: $pIC_{50}$ = 8.1 corresponds to $IC_{50}$ = 7.9 nM Table 3: not reported | Table 1: $pIC_{50}$ = 6.0 corresponds to $IC_{50}$ = 1000 nM Table 2: $pIC_{50}$ = 5.9 corresponds to $IC_{50}$ = 1259 nM Table 3: not reported | Table 1: 50 Table 2: 159 |
| Example 14 | Table 1: $pIC_{50}$ = 8.3 corresponds to $IC_{50}$ = 5.0 nM Table 2: $pIC_{50}$ = 7.8 corresponds to $IC_{50}$ = 16 nM Table 3: not reported | Table 1: $pIC_{50}$ = 6.8 corresponds to $IC_{50}$ = 158 nM Table 2: $pIC_{50}$ = 7.2 corresponds to $IC_{50}$ = 63 nM Table 3: not reported | Table 1: 32 Table 2: 4 |
| Example 39 | Table 1: $pIC_{50}$ = 8.2 corresponds to $IC_{50}$ = 6.3 nM Table 2: $pIC_{50}$ = 7.7 corresponds to $IC_{50}$ = 20 nM Table 3: $pIC_{50}$ = 9.1 corresponds to $IC_{50}$ = 0.79 nM | Table 1: $pIC_{50}$ = 6.0 corresponds to $IC_{50}$ = 1000 nM Table 2: $pIC_{50}$ = <5.0 corresponds to $IC_{50}$ = <10000 nM Table 3: $pIC_{50}$ = 5.8 corresponds to $IC_{50}$ = 1585 nM | Table 1: 159 Table 2: 500 Table 3: 2006 |
| Example 42 | Table 1: $pIC_{50}$ = 7.9 corresponds to $IC_{50}$ = 12.6 nM Table 2 and 3: not reported | Table 1: $pIC_{50}$ = 6.0 corresponds to $IC_{50}$ = 1000 nM Table 2 and 3: not reported | Table 1: 79 |

TABLE 3-continued

In vitro potencies of the structurally closest prior art compounds (Example 70, 71 and 73) in WO2016/034882 as reported therein:

| Structure Example # in WO2016/034882 | As described in WO2016/034882 (Table 1 (Method 1), Table 2 (Method A), Table 3 (Method B), page 177-180) | | |
|---|---|---|---|
| | OX1R | OX2R | OX2R IC$_{50}$/ OX1R IC$_{50}$ |
| Example 71 | Table 1 and 2: not reported Table 3: pIC$_{50}$ = 9.0 corresponds to IC$_{50}$ = 1 nM | Table 1 and 2: not reported Table 3: pIC$_{50}$ = 6.6 corresponds to IC$_{50}$ = 320 nM | Table 3: 320 |
| Example 73 | Table 1 and 2: not reported Table 3: pIC$_{50}$ = 8.8 corresponds to IC$_{50}$ = 1.6 nM | Table 1 and 2: not reported Table 3: pIC$_{50}$ < 6.0 corresponds to IC$_{50}$ > 1000 nM | Table 3: >625 |
| Example 84 | Table 1 and 2: not reported Table 3: pIC$_{50}$ = 8.7 corresponds to IC$_{50}$ = 1.9 nM | Table 1 and 2: not reported Table 3: pIC$_{50}$ = 6.0 corresponds to IC$_{50}$ = 1000 nM | Table 3: 526 |
| Example 91 | Table 1 and 2: not reported Table 3: pIC$_{50}$ = 7.6 corresponds to IC$_{50}$ = 25 nM | Table 1 and 2: not reported Table 3: pIC$_{50}$ < 5.1 corresponds to IC$_{50}$ = 7950 nM | Table 3: 318 |

Table 4a lists data on the OX1R and OX2R potencies and Table 4b shows data on the stability in MDCK efflux (assay C) and the log P (assay D) of the compounds of the present invention. These data demonstrate that compounds of the present invention are superior over the prior art compounds in terms of their OX1R potency. Moreover, they have high selectivity over the OX2R, no or low MDCK efflux and an appropriate lipophilicity (log P). These pharmacodynamic and pharmacokinetic characteristics render suitable as PET radioligands the corresponding radioisotope-labelled ($^{11}$C or $^{18}$F labelling) analogs of the compounds of the present invention.

Example 1 of the current invention differs structurally from Example 91 in WO2016/034882, the closest prior art compound, in that it contains a central N-ethyl-(propan-2-yl)amino moiety in place of N-methyl-[butan-2-yl]amino moiety. It further has a differently substituted phenyl group: it contains an additional methyl group as compared to Example 91 in WO2016/034882. Unexpectedly, these structural differences lead to an increase in OX1R potency and an increase in OX1R selectivity compared to Example 91 in WO2016/034882.

Examples 2, 3, 4, 5 and 20 of the current invention differ structurally from Example 73 in WO2016/034882, the closest prior art compound, in that they contain a central N-ethyl-(propan-2-yl)amino moiety in place of N-ethyl-[butan-2-yl]amino moiety. They further have a substituted phenyl group instead of a pyridyl group.

Examples 2 and 3 contain a phenyl group bearing the same substitution pattern as compared to a pyridyl group in Example 73 in WO2016/034882. Example 3 additionally bears a methyl group on the nitrogen atom connected to the pyrimidyl group.

Example 4 contains a methoxy group instead of a methyl group in the same position of a phenyl group, while Example 20 contains a methoxy group in a different position of the phenyl group as compared to Example 73 in WO2016/034882; and Example 5 contains a methyl group in a different position of the phenyl group as compared to Example 73 in WO2016/034882. These structural differences unexpectedly result in Examples 3, 4, 5 and 20 having an increased OX1R potency and enhanced OX1R selectivity as compared to Example 71 in WO2016/034882. Example 2 surprisingly is superior to Example 71 in WO2016/034882 with regard to OX1R potency.

Examples 9, 10 and 14 of the present invention differ structurally from Example 73 in WO2016/034882, the closest prior art compound, in that they contain a central N-ethyl-(propan-2-yl)amino moiety in place of N-ethyl-[butan-2-yl]amino moiety, and the —N-chloropyridyl group in place of —N-trifluoromethylpyrimidyl. They differ further by having a substituted phenyl group instead of a pyridyl group. Examples 9 and 10 contain a phenyl group with the same substitution pattern as compared to Example 73 in WO2016/034882. Example 9 additionally bears a methyl group on the nitrogen atom connected to the pyridyl group. Example 14 contains two methyl groups at the phenyl group in different positions as compared to Example 73 in WO2016/034882. Unexpectedly, these structural differences lead to an increase in OX1R potency for Examples 9, 10, and 14, and an increase in OX1R potency and selectivity for Examples 9 and 14 as compared to Example 73 in WO2016/034882.

Examples 6 and 8 of the present invention differ structurally from Example 14 in WO2016/034882, the closest prior art compound, in that it contains a central N-ethyl-(propan-2-yl)amino moiety in place of N-methyl-[prop-2-yl]amino moiety, and a —N-trifluoromethylpyrimidyl group in place of —N-chloropyridyl group. They further contain a methylthiazole group instead of a phenyl group. Example 6 bears a phenyl substituent, and Example 8 bears a 4-fluorophenyl substituent in the same position relative to the linker attachment as compared to Example 14 in WO2016/034882. Unexpectedly, these structural differences lead to an increase in OX1R potency and selectivity for Examples 6 and 8 as compared to Example 14 in WO2016/034882.

Example 7 of the present invention differs structurally from Example 39 in WO2016/034882, the closest prior art compound, in that it contains a central N-ethyl-(propan-2-yl)amino moiety in place of N-ethyl-[butan-2-yl]amino moiety. It further has a differently substituted phenyl group: it contains the chloro group in a different position as compared to Example 39 in WO2016/034882. Unexpectedly, these structural differences lead to an increase in OX1R potency and OX1R selectivity as compared to Example 39 in WO2016/034882.

Examples 11, 12 and 13 of the present invention differ structurally from Example 84 in WO2016/034882, the closest prior art compound, in that they contain a central N-ethyl-(propan-2-yl)amino moiety in place of N-methyl-[butan-2-yl]amino moiety and contain a —N-pyridyl instead of a —N-pyrimidine substituent. Example 12 has an additional fluoro group in a pyridyl group, and Example 13 has an additional fluoro group and a trifluoromethyl group in different positions relative to the linker attachment as compared to Example 84 in WO2016/034882. They further have a differently substituted phenyl group instead of the pyridyl group. Examples 11 and 12 contain a fluoro group in a different position relative to the linker attachment, and also lack a methyl group as compared to Example 84 in WO2016/034882. Example 13 bears a fluoro group instead of a methyl group as compared to Example 84 in WO2016/034882. Unexpectedly, these structural differences lead to an increase in OX1R potency and OX1R selectivity as compared to Example 84 in WO2016/034882.

Examples 15 and 16 of the present invention differ structurally from Example 71 in WO2016/034882, the closest prior art compound, in that they contain a central N-ethyl-(propan-2-yl)amino moiety in place of N-ethyl-[butan-2-yl]amino moiety. Example 16 additionally bears a fluoro substituent on the —N-pyridyl group.

They further differ by having a differently substituted phenyl ring instead of a pyridyl ring. Both contain a methyl group on the phenyl group instead of a fluoro substituent, and in a different position as compared to Example 71 in WO2016/034882. These structural differences unexpectedly result in an increase in OX1R potency as compared to Example 71 in WO2016/034882.

Example 17 of the present invention differs structurally from Example 1 in WO2016/034882, the closest prior art compound, in that it contains a central N-ethyl-(propan-2-yl)amino moiety in place of N-methyl-[butan-2-yl]amino moiety. A further difference lies in the phenyl group that contains a fluoro group instead of a methyl group in a different position as compared to Example 1 in WO2016/034882. Unexpectedly, these structural differences lead to an increase in OX1R potency and an increase in OX1R selectivity compared to Example 1 in WO2016/034882.

Examples 18 and 19 of the present invention differ structurally from Example 42 in WO2016/034882, the closest prior art compound, in that they contain a central N-ethyl-(propan-2-yl)amino moiety in place of N-methyl-[butan-2-yl]amino moiety. Example 18 contains an additional fluoro substituent on the N-pyridyl and Example 19 contains a —O-pyridyl instead of a —N-pyridyl group as compared to Example 42 in WO2016/034882.

Example 18 further has a differently substituted phenyl group: it contains a fluoro substituent instead of a chloro substituent in a different position as compared to Example 42 in WO2016/034882. Example 19 contains a differently substituted pyridyl group instead of the phenyl group: it contains a pyrazolyl group instead of a triazolyl group, and a trifluoromethyl substituent instead of a chloro group in a different position as compared to Example 42 in WO2016/034882. These structural differences unexpectedly result in an increase in OX1R potency and OX1R selectivity compared to Example 42 in WO2016/034882.

TABLE 4a

| Example | Structure | Assay A OX1R Kb [nM] (50 nM Orexin A concentration) | Assay B OX2R Kb [nM] (0.5 nM Orexin A concentration) | OX2R Kb/ OX1R Kb |
|---|---|---|---|---|
| Ex 91 in WO2016/ 034882 | 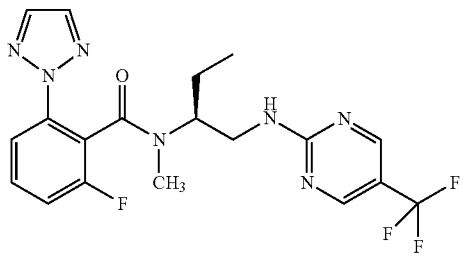 [SMILES: CC[C@@H](CNc1ncc(C(F)(F)F)cn1)N(C)C(=O)c1c(F)cccc1-n1nccn1] | 3.96 | 313.4 | 86 |
| 1 | 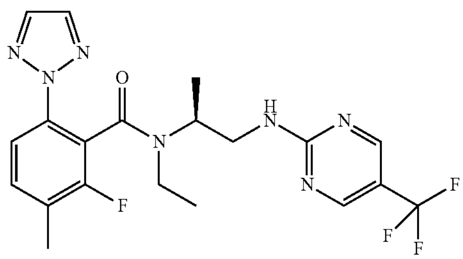 [SMILES: CCN(C(=O)c1c(-n2nccn2)ccc(C)c1F)[C@@H](C)CNc1ncc(C(F)(F)F)cn1] | 0.041 | 21.84 | 529 |
| Ex 73 in WO2016/ 034882 | 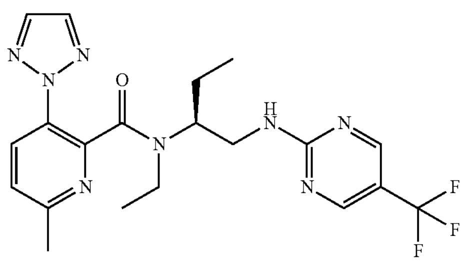 [SMILES: CC[C@@H](CNc1ncc(C(F)(F)F)cn1)N(CC)C(=O)c1nc(C)ccc1-n1nccn1] | 0.309 | 147.9 | 479 |
| 2 | 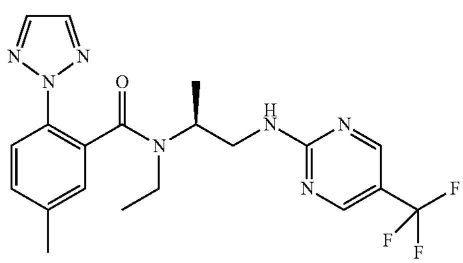 [SMILES: CCN(C(=O)c1cc(C)ccc1-n1nccn1)[C@@H](C)CNc1ncc(C(F)(F)F)cn1] | 0.011 | 4.14 | 379 |
| 3 | 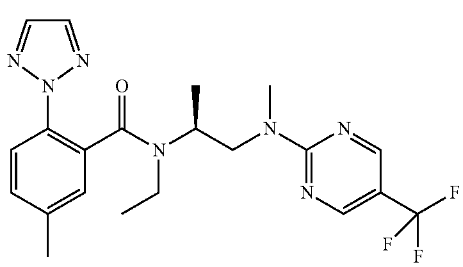 [SMILES: CCN(C(=O)c1cc(C)ccc1-n1nccn1)[C@@H](C)CN(C)c1ncc(C(F)(F)F)cn1] | 0.020 | 15.18 | 755 |

TABLE 4a-continued

Biological data of the compounds of the present invention

| Example | Structure | Assay A OX1R Kb [nM] (50 nM Orexin A concentration) | Assay B OX2R Kb [nM] (0.5 nM Orexin A concentration) | OX2R Kb/ OX1R Kb |
| --- | --- | --- | --- | --- |
| 4 | 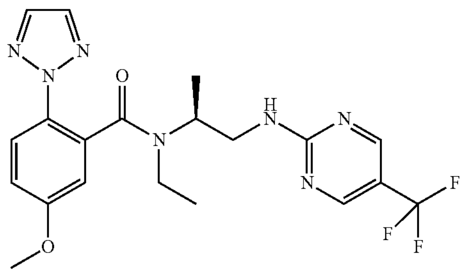 [SMILES: CCN(C(=O)c1cc(OC)ccc1-n1nccn1)[C@@H](C)CNc1ncc(C(F)(F)F)cn1] | 0.020 | 14.43 | 736 |
| 5 | 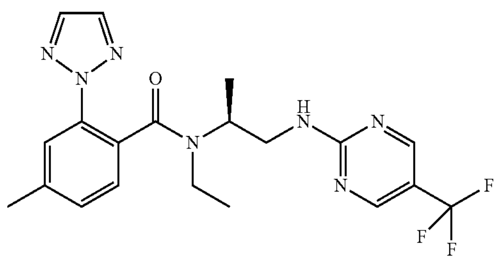 [SMILES: CCN(C(=O)c1ccc(C)cc1-n1nccn1)[C@@H](C)CNc1ncc(C(F)(F)F)cn1] | 0.012 | 21.14 | 1783 |
| 9 | 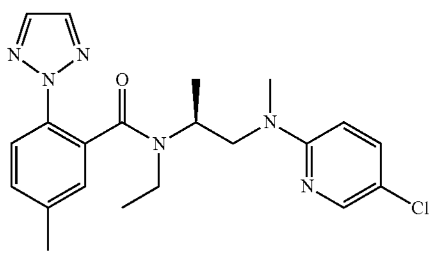 [SMILES: CCN(C(=O)c1cc(C)ccc1-n1nccn1)[C@@H](C)CN(C)c1ccc(Cl)cn1] | 0.0053 | 4.79 | 909 |
| 10 | 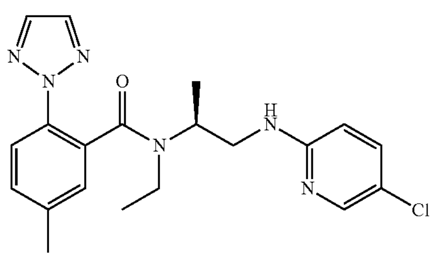 [SMILES: CCN(C(=O)c1cc(C)ccc1-n1nccn1)[C@@H](C)CNc1ccc(Cl)cn1] | 0.014 | 5.57 | 403 |
| 14 | 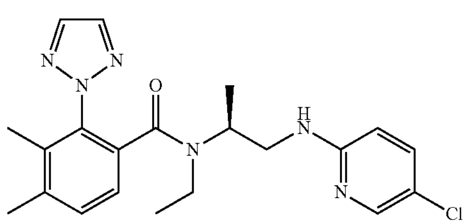 [SMILES: CCN(C(=O)c1ccc(C)c(C)c1-n1nccn1)[C@@H](C)CNc1ccc(Cl)cn1] | 0.023 | 22.94 | 1018 |

TABLE 4a-continued

Biological data of the compounds of the present invention

| Example | Structure | Assay A OX1R Kb [nM] (50 nM Orexin A concentration) | Assay B OX2R Kb [nM] (0.5 nM Orexin A concentration) | OX2R Kb/ OX1R Kb |
|---|---|---|---|---|
| 20 | 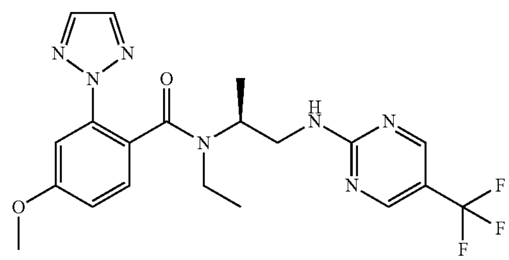 [SMILES: CCN(C(=O)c1ccc(OC)cc1-n1nccn1)[C@@H](C)CNc1ncc(C(F)(F)F)cn1] | 0.091 | 115.0 | 1264 |
| Ex 14 in WO2016/ 034882 | 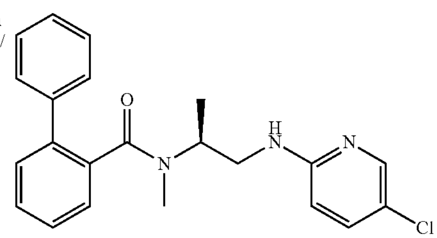 | 0.171 | 4.7 | 27 |
| 6 | 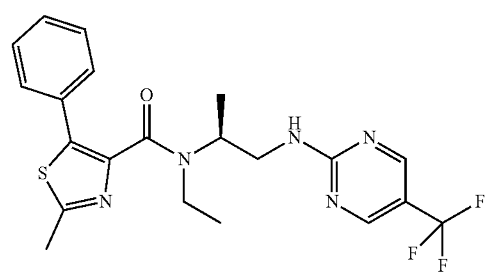 [SMILES: CCN(C(=O)c1nc(C)sc1-c1ccccc1)[C@@H](C)CNc1ncc(C(F)(F)F)cn1] | 0.013 | 7.03 | 527 |
| 8 | 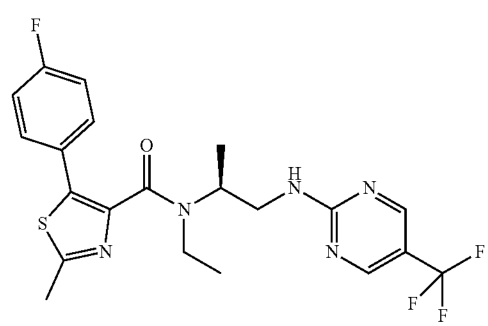 [SMILES: CCN(C(=O)c1nc(C)sc1-c1ccc(F)cc1)[C@@H](C)CNc1ncc(C(F)(F)F)cn1] | 0.022 | 7.92 | 367 |
| Ex 39 in WO2016/ 034882 | 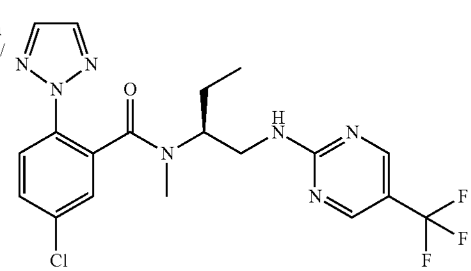 | 0.443 | 81.5 | 184 |

TABLE 4a-continued

Biological data of the compounds of the present invention

| Example | Structure | Assay A OX1R Kb [nM] (50 nM Orexin A concentration) | Assay B OX2R Kb [nM] (0.5 nM Orexin A concentration) | OX2R Kb/ OX1R Kb |
|---|---|---|---|---|
| 7 | 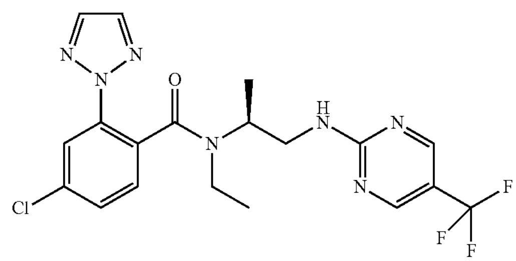 [SMILES: CCN(C(=O)c1ccc(Cl)cc1-n1nccn1)[C@@H](C)CNc1ncc(C(F)(F)F)cn1] | 0.025 | 23.19 | 922 |
| Ex 84 in WO2016/ 034882 | 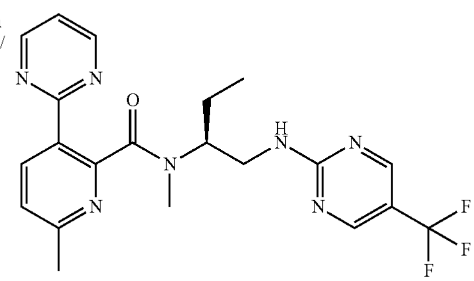 | 2.33 | 228.6 | 104 |
| 11 | 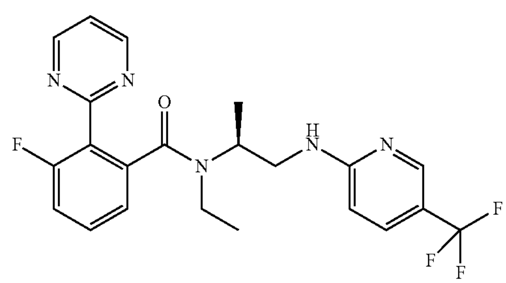 [SMILES: CCN(C(=O)c1cccc(F)c1-c1ncccn1)[C@@H](C)CNc1ccc(C(F)(F)F)cn1] | 0.015 | 3.15 | 212 |
| 12 | 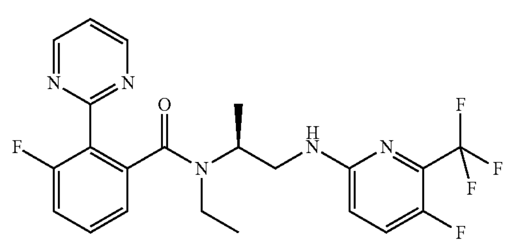 [SMILES: CCN(C(=O)c1cccc(F)c1-c1ncccn1)[C@@H](C)CNc1ccc(F)c(C(F)(F)F)n1] | 0.019 | 4.15 | 216 |
| 13 | 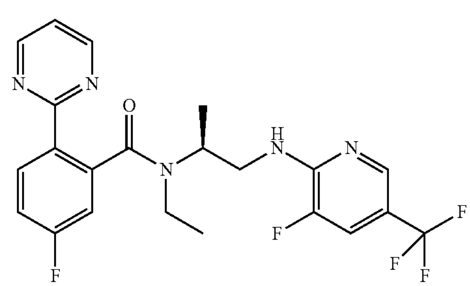 [SMILES: CCN(C(=O)c1cc(F)ccc1-c1ncccn1)[C@@H](C)CNc1ncc(C(F)(F)F)cc1F] | 0.012 | 5.16 | 438 |

TABLE 4a-continued

Biological data of the compounds of the present invention

| Example | Structure | Assay A OX1R Kb [nM] (50 nM Orexin A concentration) | Assay B OX2R Kb [nM] (0.5 nM Orexin A concentration) | OX2R Kb/ OX1R Kb |
|---|---|---|---|---|
| Ex 71 in WO2016/ 034882 | 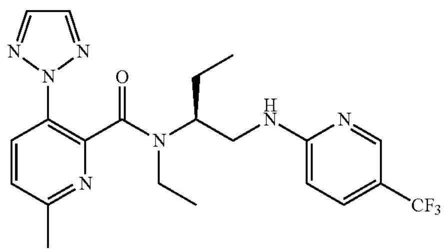 [SMILES: CC[C@@H](CNc1ccc(C(F)(F)F)cn1)N(CC)C(=O)c1nc(C)ccc1-n1nccn1] | 0.030 | 27.3 | 905 |
| 15 | 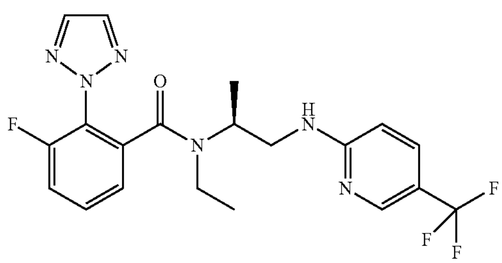 [SMILES: CCN(C(=O)c1cccc(F)c1-n1nccn1)[C@@H](C)CNc1ccc(C(F)(F)F)cn1] | 0.0044 | 3.86 | 880 |
| 16 | 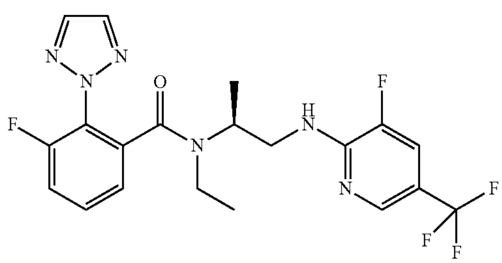 [SMILES: CCN(C(=O)c1cccc(F)c1-n1nccn1)[C@@H](C)CNc1ncc(C(F)(F)F)cc1F] | 0.014 | 7.60 | 560 |
| Ex 1 in WO2016/ 034882 | 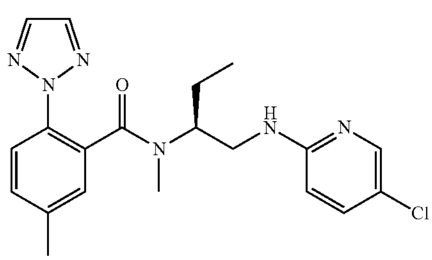 [SMILES: CC[C@@H](CNc1ccc(Cl)cn1)N(C)C(=O)c1cc(C)ccc1-n1nccn1] | 0.185 | 43.2 | 233 |
| 17 | 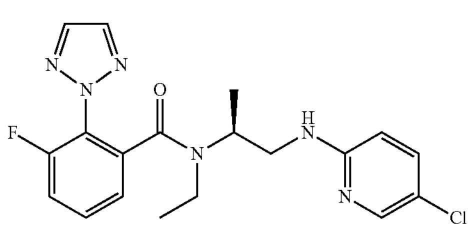 [SMILES: CCN(C(=O)c1cccc(F)c1-n1nccn1)[C@@H](C)CNc1ccc(Cl)cn1] | 0.043 | 11.44 | 268 |

TABLE 4a-continued

Biological data of the compounds of the present invention

| Example | Structure | Assay A OX1R Kb [nM] (50 nM Orexin A concentration) | Assay B OX2R Kb [nM] (0.5 nM Orexin A concentration) | OX2R Kb/ OX1R Kb |
|---|---|---|---|---|
| Ex 42 in WO2016/ 034882 | 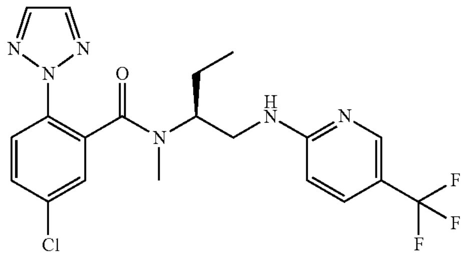 [SMILES: CC[C@@H](CNc1ccc(C(F)(F)F)cn1)N(C)C(=O)c1cc(Cl)ccc1-n1nccn1] | 0.182 | 36.2 | 199 |
| 18 | 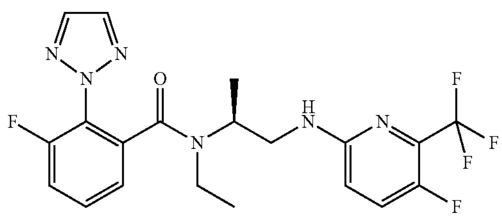 [SMILES: CCN(C(=O)c1cccc(F)c1-n1nccn1)[C@@H](C)CNc1ccc(F)c(C(F)(F)F)n1] | 0.078 | 16.30 | 209 |
| 19 | 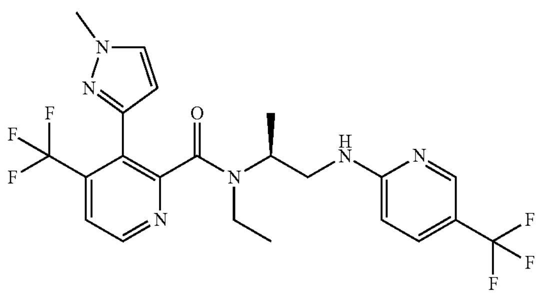 [SMILES: CCN(C(=O)c1nccc(C(F)(F)F)c1-c1ccn(C)n1)[C@@H](C)CNc1ccc(C(F)(F)F)cn1] | 0.114 | 26.2 | 230 |

TABLE 4b

MDCK efflux ratios and logP ranges of the compounds of the present invention

| | Examples |
|---|---|
| Assay C | |
| MDCK efflux ratio (BA/AB) < 3 | Examples 2, 3, 4, 6, 7, 8, 14, 15, 16, 19, 20 |
| Assay D | |
| logP = 2-4 | Examples 1-8, 11, 12, 13, 15, 16, 18, 19, 20 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (includes but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders,

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
Antidepressants
Mood stabilizers
Antipsychotics
Anxiolytics
Antiepileptic drugs
Sleeping agents
Cognitive enhancer
Stimulants
Non-stimulant medication for attention deficit hyperactivity disorder
Additional psychoactive drugs.

EXPERIMENTAL SECTION

List of Abbreviations

RT room temperature
$K_{222}$ 2,2,2-cryptand
ESI-MS electrospray ionisation mass spectrometry
CIP 2-chloro-4,5-dihydro-1,3-dimethyl-1H-imidazolium hexafluorophosphate
aq. aqueous
MS mass spectrometry
MeOH methanol
EtOH ethanol
EA ethyl acetate
DMF N,N-dimethylformamide
DMSO dimethyl sulfoxide
DCM dichloromethane
TEA triethylamine
THF tetrahydrofuran
DIPEA N,N-diisopropylethylamine
HATU 1-[bis(dimethylamino)methylene]-1H-1,2,3-triazolo[4,5-b]pyridinium 3-oxid hexafluorophosphate
TBTU O-(benzotriazol-1-yl)-N,N,N',N'-tetramethyl-uronium tetrafluoroborate
Rt retention time
h hour(s)
min minutes
sat. saturated
ACN acetonitrile
TFA trifluoroacetic acid
M molarity
N normality
HPLC high-performance liquid chromatography
HPLC-MS high-performance liquid chromatography-mass spectrometry
NMP N-Methyl-2-pyrrolidone
HPLC-Methods:
Method Name: A
Column: XBridge O18, 4.6×30 mm, 3.5 μm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |

Method Name: B
Column: Sunfire C18, 2.1×30 mm, 2.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 1.60 | 0 | 100 | 5 | 60 |
| 1.70 | 0 | 100 | 5 | 60 |

| Gradient/Solvent Time [min] | % Sol [H₂O, 0.1% TFA] | % Sol [ACN] | Flow [mL/min] | Temp [° C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: C
Column: XBridge C18, 3×30 mm, 2.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: D
Column: Xselect CSH, 2.5 μm, 4.6×50 mm
Column Supplier: Waters

| Gradient/Solvent Time [min] | % Sol [90% H₂O + 10% ACN + 0.1% HCOOH] | % Sol [90% ACN + 10% H₂O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: E
Column: Sunfire C18, 3.0×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |

Method Name: F
Column: Synergi Hydro RP100A, 2.5 μm, 3×50 mm
Column Supplier: Phenomenex

| Gradient/Solvent Time [min] | % Sol [90% H₂O + 10% ACN + 5 mM NH₄COOH] | % Sol [90% ACN + 10% H₂O] | Flow [mL/min] | Temp [° C.] |
|---|---|---|---|---|
| 0.00 | 100 | 0 | 1.2 | RT |
| 4.00 | 0 | 100 | 1.2 | RT |
| 5.30 | 0 | 100 | 1.2 | RT |
| 5.50 | 100 | 0 | 1.2 | RT |
| 6.00 | 100 | 0 | 1.2 | RT |

Method Name: G
Column: BEH C18 1.7 μm 2.1×50 mm
Column Supplier: Waters

| Gradient/Solvent Time [min] | % Sol [90% H₂O + 10% ACN + NH₄COOH 5 mM] | % Sol [90% ACN + 10% H₂O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: H
Column: XBridge C18 2.5 μm, 3.0*30 mm
Column Supplier: Waters

| Gradient/Solvent Time [min] | % Sol [Water 0.1% NH₃] | % Sol [Acetonitrile] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method Name: I
Column: Sunfire, 3×30 mm, 2.5 μm
Column Supplier: Waters

| Gradient/Solvent Time [min] | % Sol [H₂O, 0.1% TFA] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.00 | 0 | 100 | 2.2 | 60 |
| 1.25 | 0 | 100 | 3 | 60 |
| 1.40 | 0 | 100 | 3 | 60 |

HPLC traces and NMR spectra of the examples and some advanced intermediates are of increased complexity due to the fact that these compounds exist in an equilibrium of multiple rotameric forms. In the case of multiple peaks in the HPLC spectrum, the retention time of the main peak is reported.

Preparation of intermediates

Acid Intermediates:

| Acid | Name | Structure | Reference/Source |
|---|---|---|---|
| A-1 | 5-Methyl-2-[1,2,3]triazol-2-yl-benzoic acid | 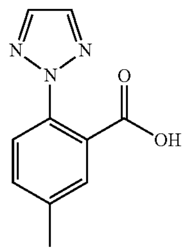 | WO2008/8518 page 31, compound A-3 |
| A-2 | 4-Methyl-2-[1,2,3]triazol-2-yl-benzoic acid | 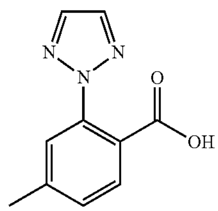 | WO2013/50938, Page 62, Intermediate B1.17 |
| A-3 | 3,4-Dimethyl-2-[1,2,3]triazol-2-yl-benzoic acid | 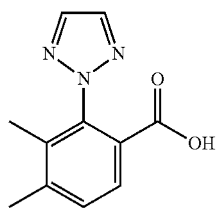 [SMILES: Cc1ccc(C(=O)O)c(-n2nccn2)c1C] | WO2013/68935, Page 58; Intermediate E-20 |
| A-4 | 3-Fluoro-2-[1,2,3]triazol-2-yl-benzoic acid | 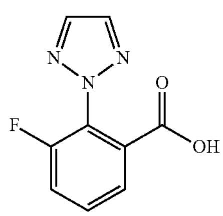 [SMILES: O=C(O)c1cccc(F)c1-n1nccn1] | WO2011/50198, Page 47, Intermediate 5 |
| A-5 | 4-Chloro-2-[1,2,3]triazol-2-yl-benzoic acid | 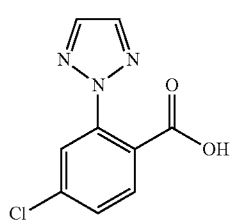 [SMILES: O=C(O)c1ccc(Cl)cc1-n1nccn1] | WO2011/50198, Page 47, Intermediate 6 |
| A-6 | 5-Methoxy-2-[1,2,3]triazol-2-yl-benzoic acid | 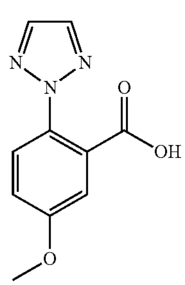 [SMILES: COc1ccc(-n2nccn2)c(C(=O)O)c1] | WO2011/50198, Page 49, Intermediate 10 |

-continued

| Acid | Name | Structure | Reference/Source |
|---|---|---|---|
| A-7 | 2-Fluoro-3-methyl-6-[1,2,3]triazol-2-yl-benzoic acid | 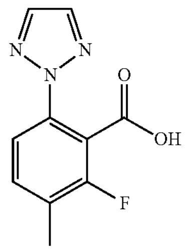 [SMILES: Cc1ccc(-n2nccn2)c(C(=O)O)c1F] | WO2012/85857 building block 34 p. 57-58 |
| A-8 | 3-Fluoro-2-pyrimidin-2-yl-benzoic acid | 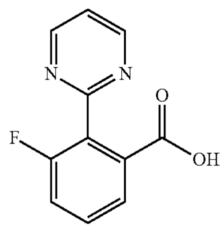 [SMILES: O=C(O)c1cccc(F)c1-c1ncccn1] | WO2011/50200, page 78, Intermediate 52 |
| A-9 | 5-Fluoro-2-pyrimidin-2-yl-benzoic acid | 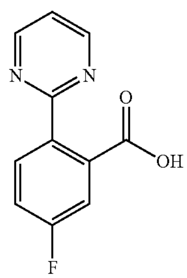 [SMILES: O=C(O)c1cc(F)ccc1-c1ncccn1] | WO2011/50200, page 54-57, Intermediate 17 |
| A-10 | 5-(4-Fluoro-phenyl)-2-methyl-thiazole-4-carboxylic acid | 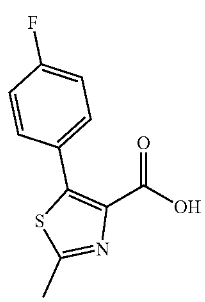 [SMILES: Cc1nc(C(=O)O)c(-c2ccc(F)cc2)s1] | commercially available from PRINCETON catalog number PBMR174109, MDL number: MFCD09907872 |
| A-11 | 2-Methyl-5-phenyl-thiazole-4-carboxylic acid | 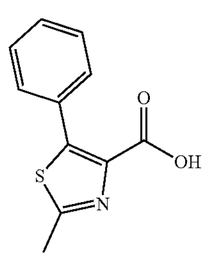 | commercially available from PRINCETON catalog number PBMR136065, MDL number: MFCD04178838 |
| A-12 | 5-Bromo-2-[1,2,3]triazol-2-yl-benzoic acid | 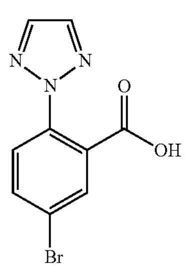 [SMILES: O=C(O)c1cc(Br)ccc1-n1nccn1] | WO2008/147518, intermediate F-1, page 47-48 |

| Acid | Name | Structure | Reference/Source |
|---|---|---|---|
| A-13 | 4-methoxy-2-[1,2,3]triazol-2-yl-benzoic acid | 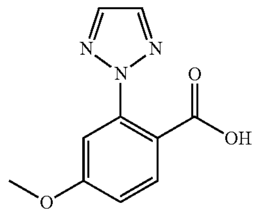 [SMILES: COc1ccc(C(=O)O)c(-n2nccn2)c1] | WO2011/50200, page 76, Intermediate 49 |

Synthesis of Amine Intermediates

N-[(2S)-2-(Ethylamino)propyl]-5-(trifluoromethyl)pyrimidin-2-amine hydrochloride B-1

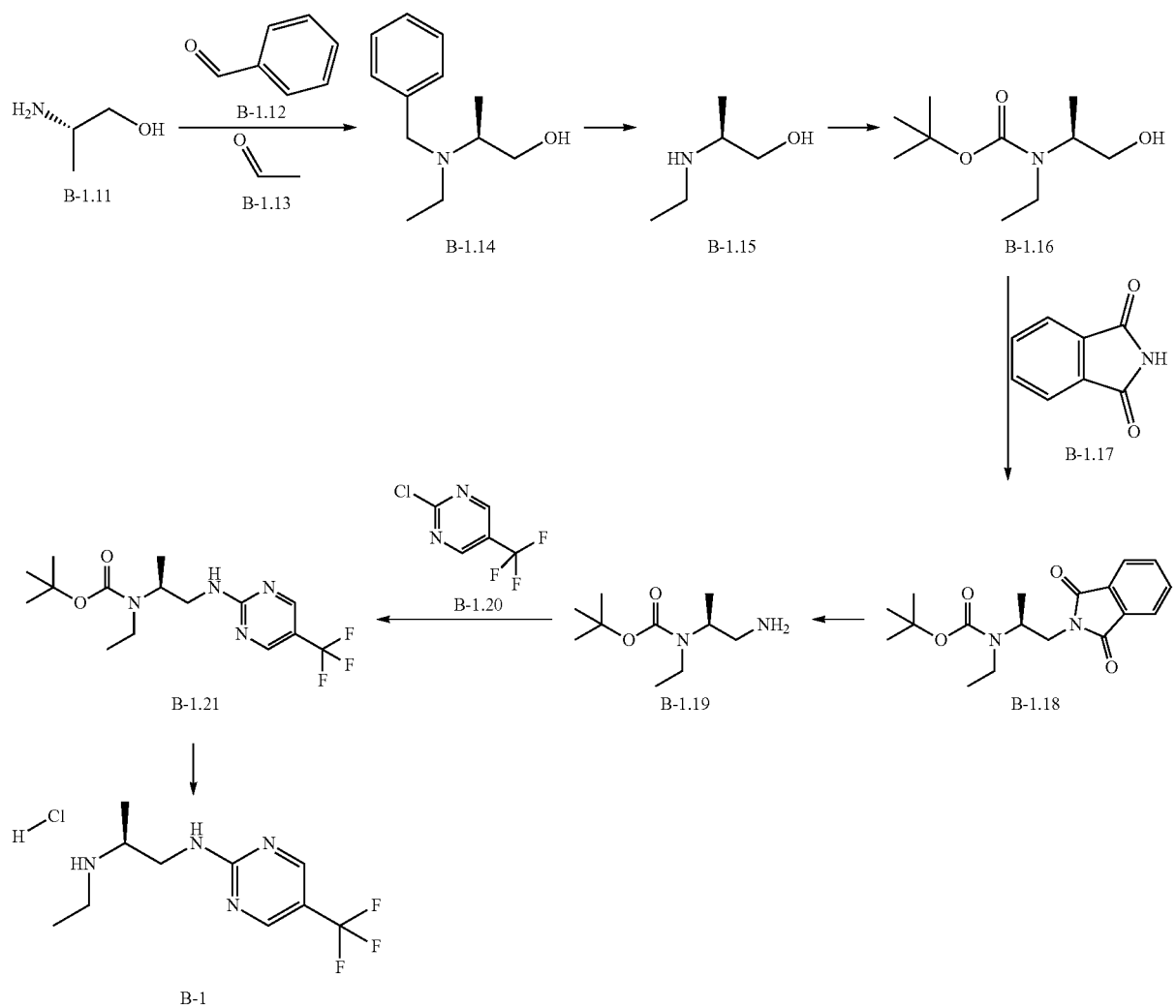

Step 1: A mixture of B-1.11 (5.0 g, 66 mmol), B-1.12 (6.8 mL, 66 mmol) in THF (180 mL) is stirred at RT for 1 h. NaBH(OAc)$_3$ (44.0 g, 0.20 mol) is added at 0° C. and the mixture is stirred at RT for 30 min. B-1.13 (11.0 mL, 0.20 mol) in THF (20 mL) is added dropwise within 10 min at 0° C. and the mixture is stirred at RT overnight. Additional B-1.13 (10 mL) is added and stirred at RT for 3 h. The precipitate is filtered and washed with THF and DCM. NaHCO$_3$ (sat. solution, 200 mL) and solid NaHCO$_3$ are added until gas formation is terminated. The water phase is extracted with DCM, dried and concentrated to provide 12 g of B-1.14. ESI-MS: 194 [M+H]$^+$; HPLC (Rt): 1.13 min (method A).

Step 2: To a mixture of B-1.14 (3.47 g, 18.0 mmol) in MeOH (4.9 mL) is added Pd/C (350 mg). The mixture is stirred at RT for 16 h under an atmosphere of hydrogen (3 bar). The mixture is filtered through a celite pad and the solvent is evaporated to afford 2.7 g of B-1.15. ESI-MS: 130 [M+H]⁺; HPLC (Rt): 0.27 min (method G).

Step 3: To a mixture of B-1.15 (3.15 g, 22.6 mmol) and di-tert-butyldicarbonate (5.42 g, 24.8 mmol) in THF (100 mL) is added portionwise DIPEA (10.0 mL, 58.4 mmol) and the mixture is stirred at RT for 3 h. The mixture is concentrated and the residue is dissolved in DCM. The mixture is washed with H₂O, NaOH (1N aq. solution), HCl (1N aq. solution) and NaCl (sat. aq. solution). The organic phase is dried and concentrated. The crude product is purified by flash column chromatography on silica gel (using a solvent gradient from 100% cyclohexane to 60% cyclohexane and 40% EA) to afford 4.5 g of B-1.16. ESI-MS: 204 [M+H]⁺; HPLC (Rt): 0.92 min (method G).

Step 4: To a mixture of B-1.16 (4.50 g, 22.1 mmol), B-1.17 (5.00 g, 34.0 mmol) and PPh₃ (8.90 g, 33.9 mmol) in dry THF (80 mL) at 0° C. and under a nitrogen atmosphere is added dropwise DIAD (6.00 mL, 33.2 mmol). The mixture is stirred at RT for 16 h. The mixture is concentrated, the residue is treated with H₂O and extracted with EA. The organic layer is separated, dried and concentrated. The residue is purified by flash column chromatography on silica gel (using a solvent mixture of hexane/EA/MeOH 70/30/1) to get 4.4 g of B-1.18. ESI-MS: 333 [M+H]⁺; HPLC (Rt): 1.25 min (method G).

Step 5: MeNH₂ (33% in EtOH, 20 mL) is added to B-1.18 (1.20 g, 3.61 mmol) at RT. The mixture is stirred for 20 h, cooled in ice-water and the solid is filtered and washed with cold EtOH. The filtrate is concentrated and the residue is treated with cold citric acid (10% aq. solution) and extracted with EA. The organic layer is separated. The pH of the aq. phase is adjusted to pH 10-11 with NH₄OH and extracted with EA. The organic layer is dried and concentrated to afford 650 mg of B-1.19. ESI-MS: 203 [M+H]⁺; HPLC (Rt): 0.65 min (method G).

Step 6: To a stirred mixture of B-1.19 (1.88 g, 9.29 mmol) and DIPEA (2.50 mL, 14.6 mmol) in NMP (20 mL) is added at RT under a nitrogen atmosphere B-1.20 (2.20 g, 12.1 mmol). The mixture is heated by microwave to 100° C. for 30 min. The cold mixture is poured into H₂O and extracted with EA. The organic phase is washed with citric acid (10% aq. solution) and H₂O. The organic layer is dried and concentrated. The residue is purified by flash column chromatography on silica gel (using a solvent mixture of hexane/EA 80/20) to get 2.7 g of B-1.21. ESI-MS: 349 [M+H]⁺; HPLC (Rt): 1.34 min (method G).

Step 7: HCl (4 M in dioxane, 40 mL) is added to a mixture of B-1.21 (5.50 g, 15.8 mmol) in dioxane (10 mL) at RT and the mixture is stirred for 2 h. The mixture is concentrated and the residue is treated with EA. The solid is filtered to afford 3.5 g of B-1. ESI-MS: 249 [M+H]⁺; HPLC (Rt): 0.63 min (method G).

N-[(2S)-2-(Ethylamino)propyl]-5-chloro-pyridin-2-amine hydrochloride B-2

Intermediate B-2 was synthesized in analogy to the above described procedure using the corresponding 5-Chloro-2-fluoro-pyridine. ESI-MS: 214 [M+H]⁺; HPLC (Rt): 0.32 min (Method B)

N-[(2S)-2-(Ethylamino)propyl]-5-(trifluoromethyl)pyrazin-2-amine hydrochloride B-3

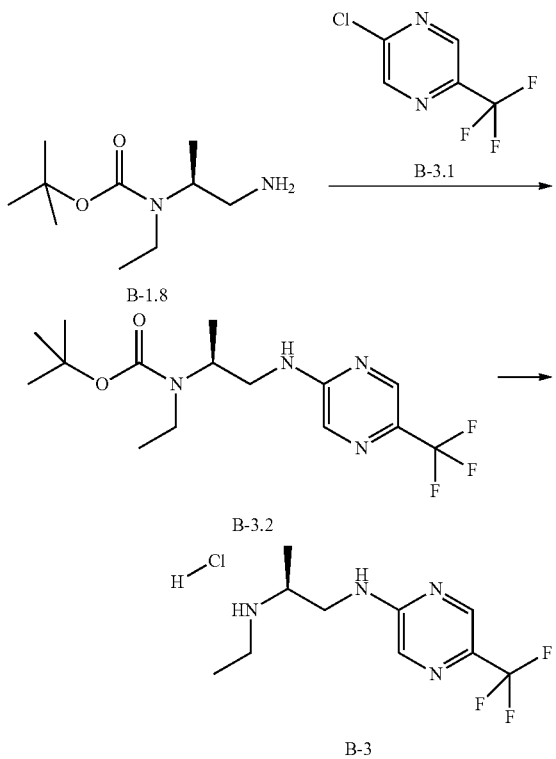

Step 1: To a stirred solution of B-1.8 (300 mg, 1.33 mmol) and DIPEA (0.51 mL, 2.98 mmol) in NMP (10 mL) B-3.1 (350 mg, 1.92 mmol) is added at RT under a nitrogen atmosphere. The mixture is stirred in a microwave at 100° C. for 30 min. The reaction is poured into water and extracted with EA. The organic phase is washed with citric acid (aq. solution) and water. The organic layer is dried and concentrated. The residue is purified by flash column chromatography on silica gel (using a solvent mixture of hexane/EA 80/20) to afford 290 mg of B-3.2. ESI-MS: 349 [M+H]⁺; HPLC (Rt): 1.32 min (Method G)

Step 2: HCl (4 M in dioxane, 5.0 mL) is added to B-3.2 (270 mg, 0.78 mmol) and the mixture is stirred at RT for 2 h. The solvent is removed to afford 220 mg of B-3. ESI-MS: 249 [M+H]⁺; HPLC (Rt): 0.64 min (Method G)

5-Chloro-N-[(2S)-2-(ethylamino)propyl]-N-methyl-pyridin-2-amine hydrochloride B-4

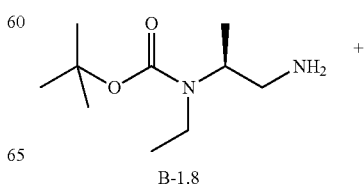

39
-continued

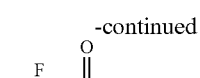

B-4.1

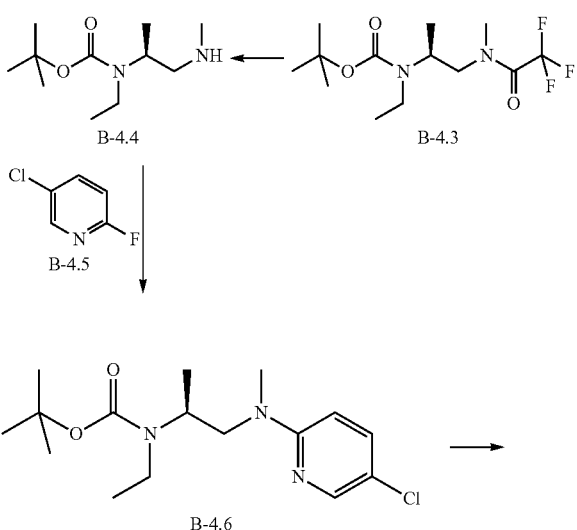

Step 1: To a stirred mixture of B-1.8 (855 mg, 3.50 mmol) in DCM (10 mL) at 0° C. is added TEA (540 µL, 3.90 mmol) and B-4.1 (540 µL, 3.90 mmol). The mixture is stirred at RT for 1 h. Another portion of TEA (540 µL, 3.90 mmol) and B-4.1 (540 µL, 3.90 mmol) is added and the mixture stirred at RT for 3 h. The mixture is diluted with DCM and the organic layer is washed with HCl (1M aq. solution) and NaOH (1M aq. solution). The organic phase is dried and concentrated to afford 1.3 g of B-4.2. ES+/−: 299 [M+H]+; HPLC (Rt): 0.75 min (method B).

Step 2: To a mixture of B-4.2 (1.28 g, 3.40 mmol) in DMF (10 mL) under a nitrogen atmosphere at 0° C. is added NaH (60% in mineral oil, 165 mg, 4.10 mmol) and the mixture is stirred for 20 min. MeI (254 µL, 4.10 mmol) is added and the mixture is stirred at RT overnight. Ice water is added and the aq. phase extracted with DCM. The organic layer is dried and concentrated to afford 791 mg of B-4.3. ES+/−: 213 [M+H]+-(BOC); HPLC (Rt): 0.80 min (method B).

Step 3: A mixture of B-4.3 (790 mg, 2.50 mmol) and NaOH (2N aq. Solution, 2.4 mL, 4.8 mmol) in MeOH (10 mL) is stirred at RT overnight. DCM is added and the organic layer washed with water, dried and concentrated to afford 519 mg of B-4.4. ES+/−: 217 [M+H]+; HPLC (Rt): 0.39 min (method B).

Step 4: A mixture of B-4.4 (100 mg, 0.46 mol), B-4.5 (56.0 µL, 0.55 mmol) and DIPEA (239 µL, 1.40 mmol) in NMP (2.0 mL) is heated at 130° C. for 40 h. The mixture is cooled and directly purified by HPLC-MS (using a solvent gradient H2O/ACN with NH4OH) to provide 28 mg of B-4.6. ES+/−: 328 [M+H]+; HPLC (Rt): 0.68 min (method B).

Step 5: HCl (4 M in dioxane, 105 µL) is added to a mixture of B-4.6 (37.5 mg, 0.08 mmol) in MeOH (1.0 mL). The mixture is stirred at RT for 3 h and concentrated to afford 25 mg of B-4. ES+/−: 228 [M+H]+; HPLC (Rt): 0.39 min (method B).

N-[(2S)-2-(Ethylamino)propyl]-N-methyl-5-(trifluoromethyl)pyrimidin-2-amine hydrochloride B-5

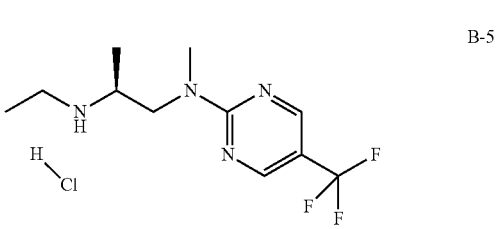

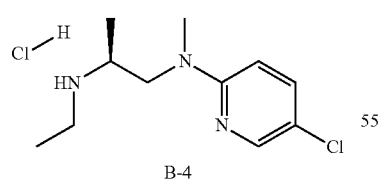

Intermediate B-5 was synthesized in analogy to the above described procedure using the corresponding 2-fluoro-5-(trifluoromethyl)-pyrimidine or 2-chloro-5-(trifluoromethyl)-pyrimidine. ESI-MS: 263 [M+H]+; HPLC (Rt): 0.41 min (Method B)

Synthesis of Amine Intermediates

N-[(2S)-1-Aminopropan-2-yl]-N-ethyl-3-fluoro-2-(pyrimidin-2-yl)benzamide C-1

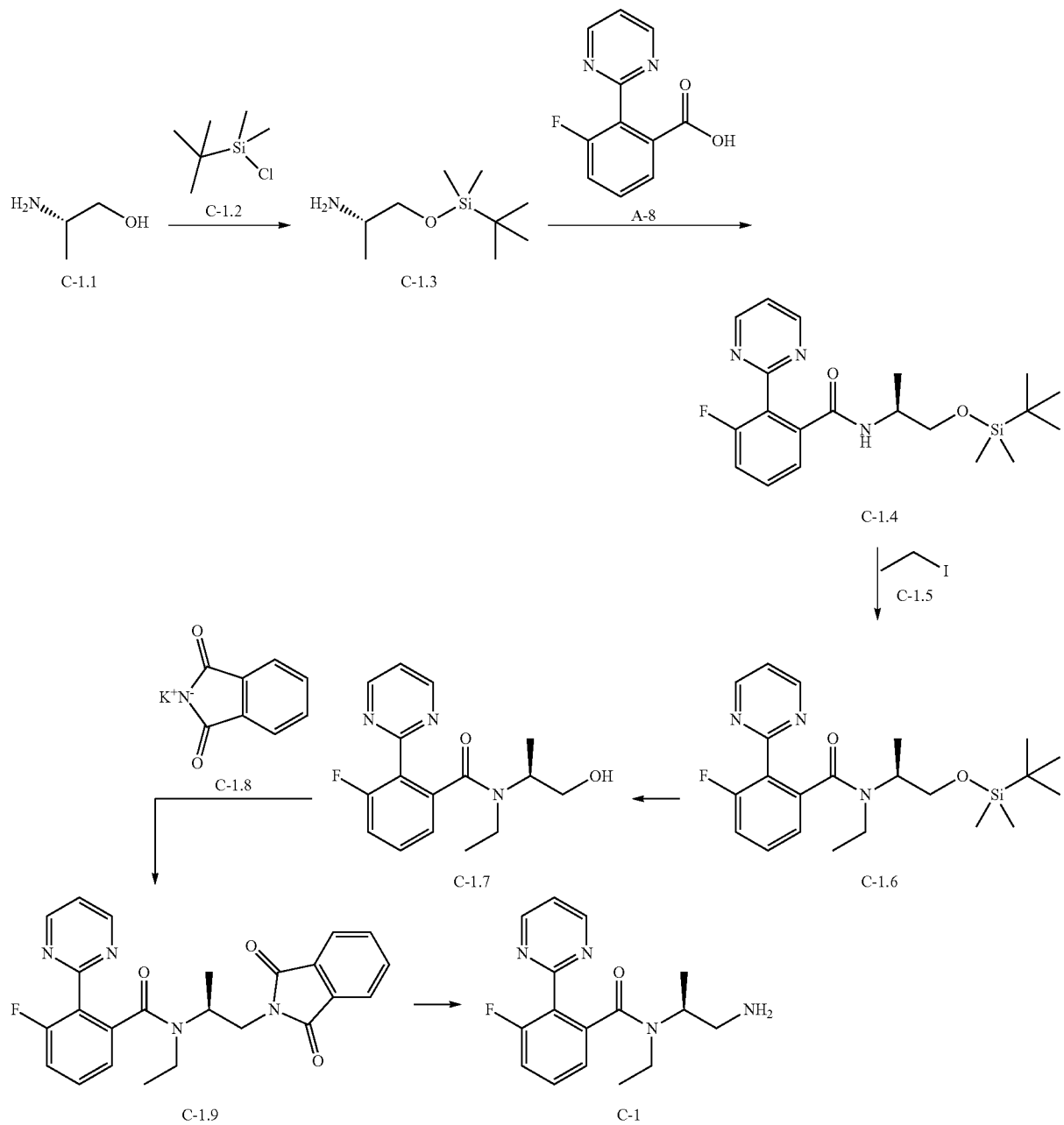

Step 1: A mixture of C-1.2 (10 g, 67 mmol) in DCM (30 mL) is added dropwise to a stirred mixture of C-1.1 (5.0 g, 67 mmol) and TEA (19.0 mL, 0.13 mol) in DCM (70 mL). The mixture is stirred at RT overnight, then a NH$_4$Cl (sat. aq. solution) is added and the aqueous phase extracted with DCM. The organic phase is dried and concentrated to afford 10 g of C-1.3. ESI-MS: 189 [M+H]$^+$; HPLC (Rt): 0.84 min (method G).

Step 2: To a mixture of A-9 (2.49 g, 11.4 mmol) in dry DMF (40 mL) under a nitrogen atmosphere is added DIPEA (5.8 mL, 34 mmol) and HATU (5.7 g, 15 mmol) and the mixture is stirred for 10 min. C-1.3 (2.4 g, 13 mmol) is added and the mixture is stirred at RT for 16 h. The mixture is treated with water and the aqueous phase extracted with EA. The organic phase is separated, washed with NaHCO$_3$ solution and citric acid (5% aq. solution), dried and concentrated. The residue is purified by flash column chromatography on silica gel (using hexane/EA 50/50) to obtain 2.7 g of C-1.4. ESI-MS: 389 [M+H]$^+$; HPLC (Rt): 1.30 min (method G).

Step 3: NaH (60% in mineral oil, 19.0 mg, 0.77 mmol) is added to a stirred mixture of C-1.4 (200 mg, 0.51 mmol) and C-1.5 (160 mg, 83.0 µL, 1.00 mmol) in dry DMF (3 mL) at 0° C. under a nitrogen atmosphere. The mixture is stirred at RT for 2 h. Water is added and the aqueous phase extracted with Et$_2$O. The organic layer is dried and concentrated to afford 200 mg of C-1.6. ESI-MS: 418 [M+H]$^+$; HPLC (Rt): 1.51 min (method G).

Step 4: TBAF (765 mg, 0.86 mL, 0.86 mmol) is added to a stirred mixture of C-1.6 (200 mg, 0.43 mmol) in THF (5.0 mL) under stirring at 0° C. The mixture is stirred at 0° C. for 30 min, concentrated and the residue purified by flash column chromatography on silica gel (using a solvent gradient from 100% DCM to 97% DCM/3% MeOH) to afford 130 mg of C-1.7. ESI-MS: 304 [M+H]$^+$; HPLC (Rt): 0.68 min (method G).

Step 5: Methanesulfonylchloride (30.0 µL, 0.39 mmol) is added to a stirred mixture of C-1.7 (100 mg, 0.33 mmol) and DIPEA (70.0 µL, 0.41 mmol) in dry DCM at −10° C. After 2 h the reaction is treated with water. The organic phase is separated, dried and concentrated under reduced pressure without heating. To the residue is added C-1.8 (70.0 mg, 0.38 mmol) and DMF at RT under stirring. After 1 h the reaction is poured into water and extracted with EA. The organic layer is separated, dried and concentrated. The residue is purified by flash column chromatography on silica gel (using hexane/EA/MeOH 50/50/1) to afford 75 mg of C-1.9. ESI-MS: 433 [M+H]$^+$; HPLC (Rt): 3.71 min (method F).

Step 6: N$_2$H$_4$.H$_2$O (30.0 µL, 0.60 mmol) is added to a mixture of C-1.9 (60.0 mg, 0.14 mmol) in EtOH (3.0 mL) at RT. The mixture is stirred for 20 h. The mixture is poured into ice-water and the solid is filtered washing with cold EtOH. The solvent is evaporated and the residue is treated with cold citric acid (10% aq. solution). The mixture is extracted with EA. The organic phase is separated, the water phase is treated with NH$_4$OH and extracted with EA. Organic layer is separated, dried and concentrated to get 30 mg of C-1. ES+/−: 303 [M+H]$^+$; HPLC (Rt): 0.58 min (method G).

Alternative Route to C-1 from C-1.7

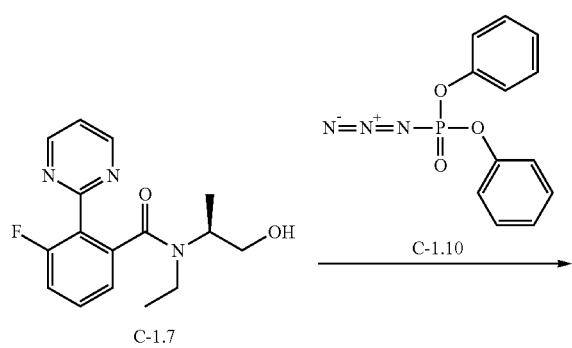

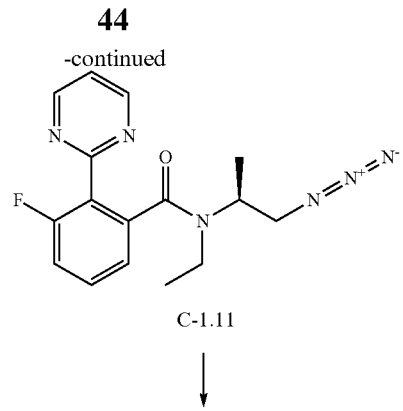

Step 1: To a stirred mixture of C-1.7 (100 mg, 0.33 mmol) and DBU (100 µL, 0.67 mmol) in dry THF (4.0 mL) at RT under a nitrogen atmosphere is added C-1.10 (90.0 µL, 0.42 mmol). After 16 h the mixture is concentrated and the residue is purified by flash column chromatography on silica gel (using hexane/EA/MeOH 80/20/1) to afford 80 mg of C-1.11. ESI-MS: 329 [M+H]$^+$; HPLC (Rt): 0.94 min (method G).

Step 2: PPh$_3$ (160 mg, 0.61 mmol) is added to a stirred mixture of C-1.11 (80.0 mg, 0.24 mmol) in THF (5.0 mL) and water (0.24 mL) at RT under a nitrogen atmosphere. After 16 h the mixture is concentrated and the residue is treated with HCl (1M aq. solution) and the aqueous phase is washed with EA. The aqueous phase is treated with NH$_4$OH (aq. solution) until pH 10-11 and extracted with DCM. The organic layer is separated, dried and concentrated to afford 65 mg of C-1. ES+/−: 303 [M+H]$^+$; HPLC (Rt): 0.58 min (method G).

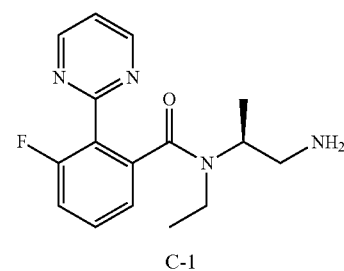

N-[(2S)-1-Aminopropan-2-yl]-N-ethyl-3-fluoro-2-(2H-1,2,3-triazol-2-yl)benzamide C-2

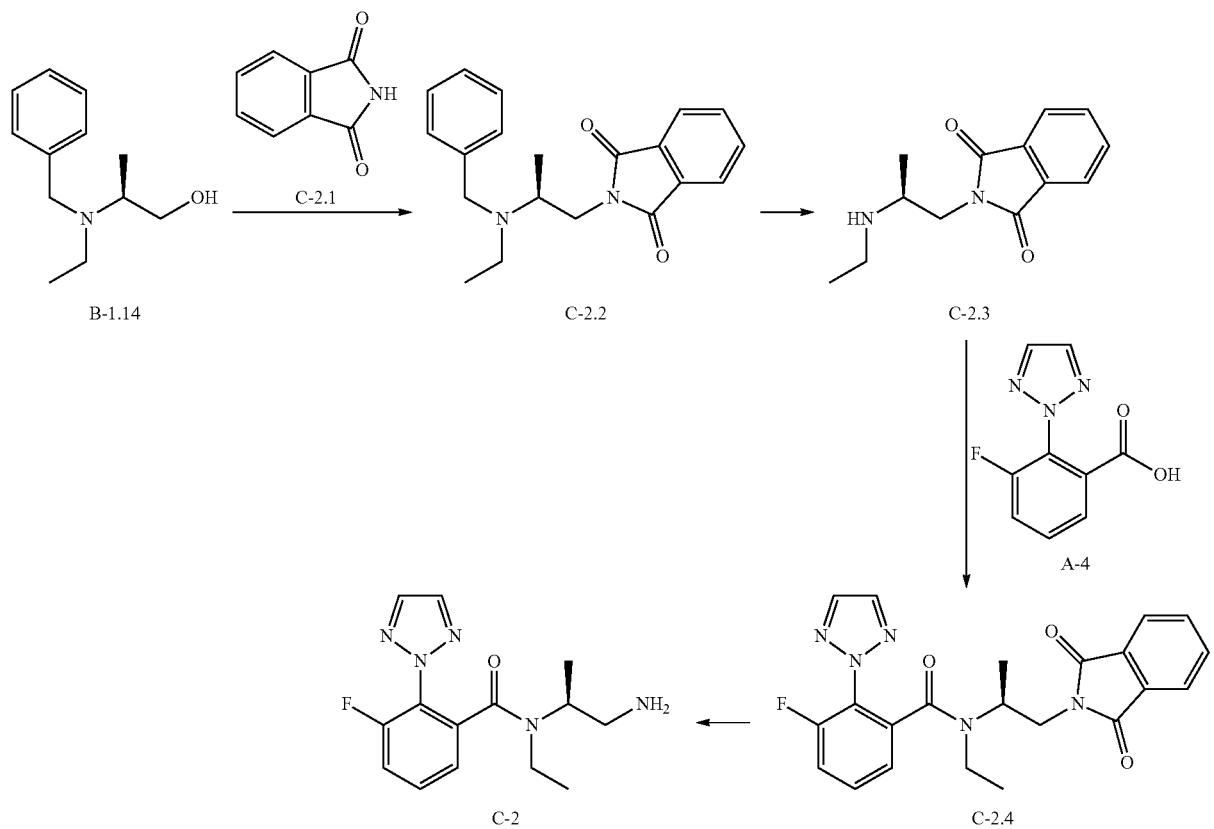

Step 1: To a mixture of B-1.14 (10.0 g, 50 mmol) and C-2.1 (7.60 g, 50 mmol) in THF (150 mL) is added PPh$_3$ (13.6 g, 50 mmol). Then DIAD (8.80 g, 50 mmol) is added dropwise at 0° C. The mixture is stirred at RT for 12 h. The reaction mixture is concentrated and the residue is purified by flash column chromatography on silica gel (using petroleum ether/EA from 20/1 to 10/1) to afford 10 g of C-2.2.

Step 2: To a mixture of C-2.2 (2.0 g, 10 mmol) in MeOH (30 mL) is added Pd/C (1.0 g). The mixture is stirred at 20° C. for 12 h under an atmosphere of hydrogen (50 psi). The mixture is filtered and the filtrate is concentrated to afford 800 mg of C-2.3.

Step 3: To a mixture of C-2.3 (2.50 g, 9.30 mmol) in dry ACN (50 mL) is added A-2 (2.30 g, 11.0 mmol), DIPEA (4.8 mL, 28 mmol) and CIP (3.1 g, 11 mmol) and the mixture is stirred at RT for 2 h. Another portion of A-4 (200 mg) and CIP (500 mg) are added and the reaction is stirred for another 2 h. Then another portion of DIPEA (1.5 mL) and CIP (300 mg) are added and the reaction is stirred for 2 h. Water (70 mL) is added to the reaction mixture is stirred for 1 h. The precipitate is filtered and dried. The mother liquid is extracted with EA, dried and concentrated. The residue is purified by prep. HPLC (using a solvent gradient H$_2$O/ACN with NH$_4$OH) and combined with the dried solid to provide 3.4 g of C-2.4. ESI pos.+neg. (Loop-Inj.) [M+H]$^+$: 422; HPLC (Rt): 0.97 min (method C).

Step 5: To a mixture of C-2.4 (3.4 g, 8.0 mmol) in EtOH (100 mL) at RT is added N$_2$H$_4$·H$_2$O (1.2 mL, 20 mmol) and the reaction is stirred overnight. Another portion of N$_2$H$_4$·H$_2$O (0.50 mL) is added and the reaction is stirred at 60° C. for 2 h. The solid is filtered. The filtrate is concentrated and the residue is taken up in EA and the organic phase extracted with HCl (1 M aq. solution). The acidic aqueous layer is washed with EA, then the pH is adjusted with NH$_4$OH (25% aq. solution) to pH=10. The aqueous phase is extracted with EA, dried and concentrated to afford 2.1 g of C-2. ESI pos.+neg. (Loop-Inj.) [M+H]$^+$: 292 [M+H]$^+$; HPLC (Rt): 0.70 min (method I).

N-[(2S)-1-Aminopropan-2-yl]-N-ethyl-5-fluoro-2-(pyrimidin-2-yl)benzamide C-3

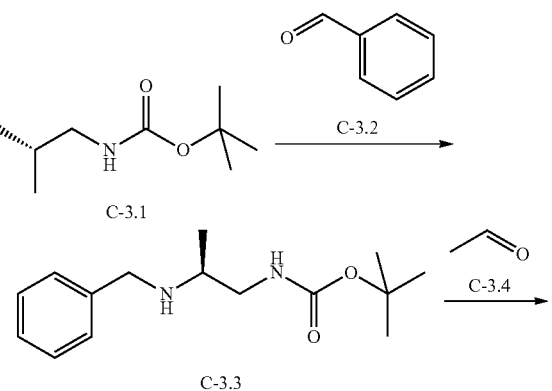

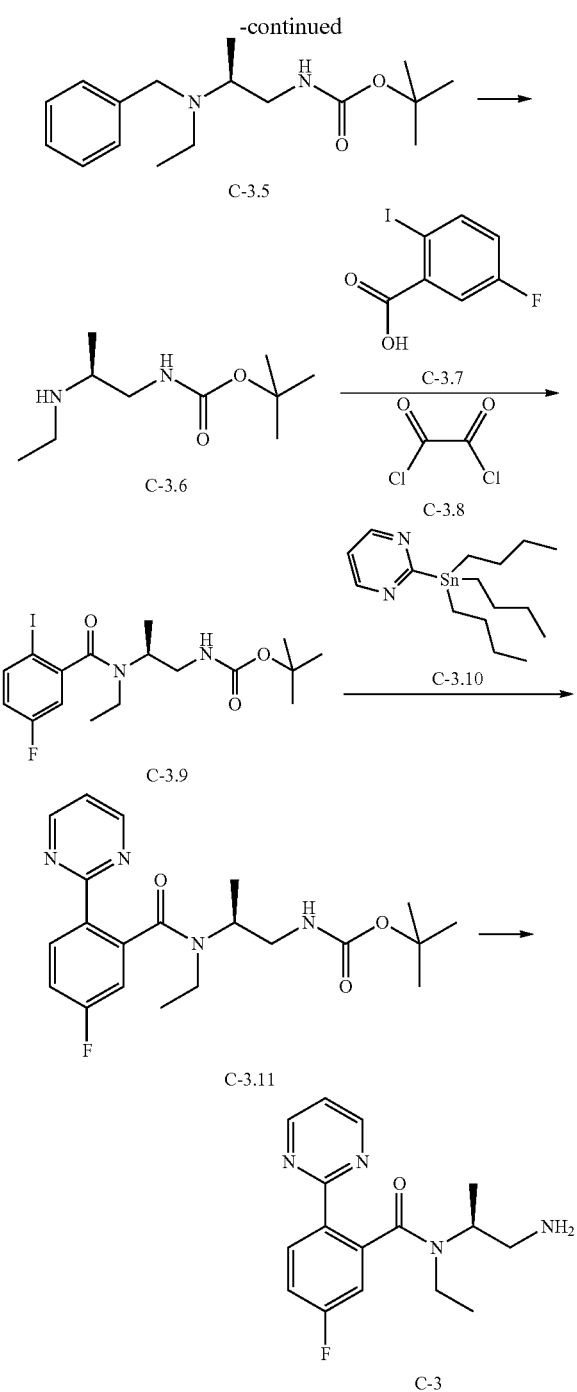

Step 1: Under a nitrogen atmosphere C-3.1 (7.00 g, 40.2 mmol) is dissolved in dry MeOH (135 mL) and C-3.2 (4.08 mL, 40.2 mmol) is added. The solution is stirred for 2 h. The mixture is then cooled to 0° C. and NaBH$_4$ (4.56 g, 0.12 mol) is added portionwise and the mixture is stirred at RT overnight. The reaction is cooled to 0° C. and is acidified with 1 N HCl. The solvent is evaporated and the aq. solution is basified with NaOH (32% aq. solution) and the product is extracted with DCM. The organic phase is separated, dried and concentrated to afford 4.6 g of C-3.3. ES+/−: 265 [M+H]$^+$; HPLC (Rt): 0.88 min (method G).

Step 2: C-3.3 (3.0 g, 30.6 mmol) is dissolved in dry MeOH (60 mL), C-3.4 (1.73 mL, 30.6 mmol) is added and the mixture is stirred at RT for 2 h. The solvent is evaporated and the residue is dissolved in dry THF (60 mL) and NaBH(OAc)$_3$ (8.66 g, 40.8 mmol) is added and the mixture is heated to reflux overnight. NH$_4$Cl (sat. aq. solution) is added and the product is extracted with EA. The organic phase is dried and concentrated. The residue is purified by flash column chromatography on silica gel (using a solvent gradient from cyclohexane/EA 90/10 to 40/60) to afford 1.9 g of C-3.5. ES+/−: 293 [M+H]$^+$; HPLC (Rt): 1.28 min (method G).

Step 3: C-3.5 (1.85 g, 5-69 mmol) is dissolved in MeOH (50 mL) and Pd/C (120 mg, 0.11 mmol) is added and the mixture is stirred under an atmosphere of hydrogen (3 bar) for 3 h. The mixture is filtered through a celite pad which is washed with MeOH and the solvent is evaporated to afford 1.1 g of C-3.6. ES+/−: 203 [M+H]$^+$; HPLC (Rt): 0.63 min (method G).

Step 4: To a stirred suspension of C-3.7 (1.50 g, 5.64 mmol) in dry DCM (8.33 mL) C-3.8 (5.64 mL, 11.3 mmol) and a drop of DMF is added and the mixture is stirred at RT for 1 h. The solvent is evaporated and the residue is dissolved in dry DCM (6.7 mL). This mixture is slowly added to a stirred mixture of C-3.6 (1.04 g, 5.13 mmol) and DIPEA (3.90 mL, 22.6 mmol) in dry DCM (10 mL) at 0° C. The reaction is stirred at RT overnight. H$_2$O is added and the organic phase is separated, washed with NH$_4$Cl (aq. solution) and KHCO$_3$ (aq. solution). The organic layer is dried and concentrated. The residue is purified by flash column chromatography on silica gel (using a solvent gradient from 100% cyclohexane to 80% cyclohexane and 20% EA) to afford 914 mg of C-3.9. ES+/−: 451 [M+H]$^+$; HPLC (Rt): 1.17 min (method G).

Step 5: C-3.9 (914 mg, 1.93 mmol), C-3.10 (980 μL, 3.09 mmol), CuI (36.7 mg, 0.19 mmol), CsF (589 mg, 3.88 mmol) and Pd(PPh$_3$)$_4$ (223 mg, 0.19 mmol) are dissolved in dry DMF (7.0 ml) and the mixture is stirred in a microwave at 130° C. for 15 min. Water is added and the product is extracted with EA. The organic phase is dried and concentrated. The crude product is purified by flash column chromatography on silica gel (using a solvent gradient from cyclohexane/EA 3/7 to 100% EA) to afford 477 mg of C-3.11. ES+/−: 403 [M+H]$^+$; HPLC (Rt): 1.02 min (method G).

Step 5: To a mixture of C-3.11 (477 mg, 1.19 mmol) in MeOH (6.0 mL) HCl (4 M aq. solution, 7.41 mL, 29.6 mmol) is added at 0° C. The mixture is stirred at RT for 1 h. The solvent is removed under reduced pressure and the residue is purified by preparative HPLC-MS (using a solvent gradient H$_2$O/ACN with NH$_4$OH) to afford 330 mg of C-3. ES+/−: 303 [M+H]$^+$; HPLC (Rt): 2.98 min (method F).

Preparation of Compounds of the Present Invention

The synthesis of Examples 1-20 containing a short-lived positron-emitting radionuclide such as $^{11}$C or $^{18}$F is performed in adaptation of the procedures described below based on radiochemistry described in the literature (e.g. see P. W. Miller et al. in Angewandte Chemie (International Ed.) 2008, 47, 8998-9033.)

Example 2

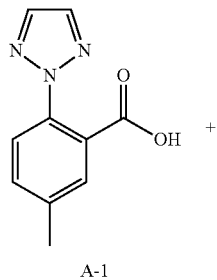

A-1

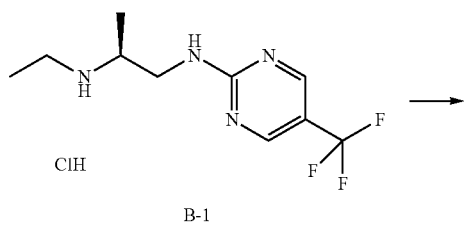

B-1

Example 2

To a mixture of A-1 (65 mg, 0.32 mmol) and DIPEA (206 μL, 1.21 mmol) in dry ACN (1.5 mL) at RT is added CIP (93 mg, 0.33 mmol) and B-1 (108 mg, 0.30 mmol) and the reaction is stirred overnight. Water (0.5 mL) and MeOH (0.5 mL) are added, the mixture is filtered and the filtrate is purified by preparative LCMS (using a solvent gradient $H_2O$/ACN with $NH_4OH$) to afford 93 mg of Example 2. ESI-MS: 434 $[M+H]^+$; HPLC (Rt): 0.74 min (method B).

The following examples are prepared in analogy to the above described procedure using the corresponding acid (see Acid Intermediates) and amine (see Amine Intermediates) as described before, adjusting the reaction time to 2 h in Example 4, 5 and 20, and using HATU and DMF in Example 20.

| Example | Structure | ESI-MS $[M + H]^+$ | HPLC (Rt) [min] | HPLC Method |
|---|---|---|---|---|
| 4 | 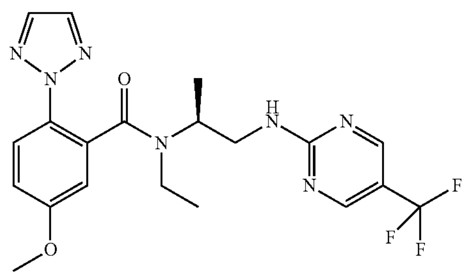 [SMILES: CCN(C(=O)c1cc(OC)ccc1-n1nccn1)[C@@H](C)CNc1ncc(C(F)(F)F)cn1] | 450 | 1.04 | C |
| 5 | 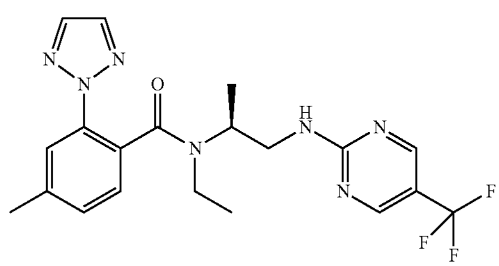 [SMILES: CCN(C(=O)c1ccc(C)cc1-n1nccn1)[C@@H](C)CNc1ncc(C(F)(F)F)cn1] | 434 | 1.07 | C |
| 6 | 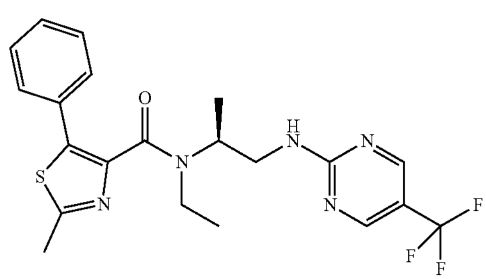 [SMILES: CCN(C(=O)c1nc(C)sc1-c1ccccc1)[C@@H](C)CNc1ncc(C(F)(F)F)cn1] | 450 | 0.91 | H |

-continued

| Example | Structure | ESI-MS [M + H]+ | HPLC (Rt) [min] | HPLC Method |
|---|---|---|---|---|
| 7 | 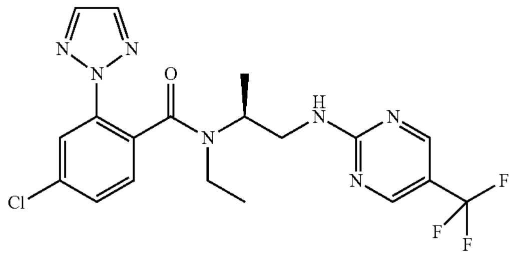 [SMILES: CCN(C(=O)c1ccc(Cl)cc1-n1nccn1)[C@@H](C)CNc1ncc(C(F)(F)F)cn1] | 454 | 0.88 | H |
| 8 | 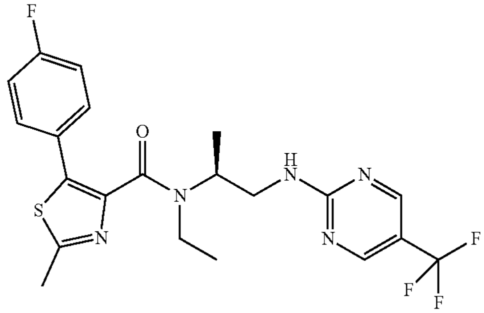 [SMILES: CCN(C(=O)c1nc(C)sc1-c1ccc(F)cc1)[C@@H](C)CNc1ncc(C(F)(F)F)cn1] | 468 | 0.92 | H |
| 20 | 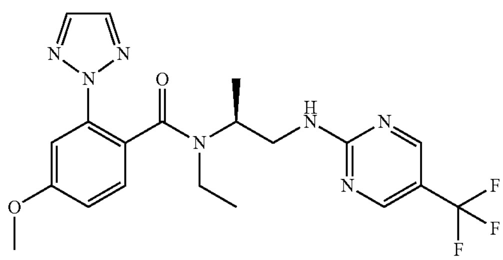 [SMILES: CCN(C(=O)c1ccc(OC)cc1-n1nccn1)[C@@H](C)CNc1ncc(C(F)(F)F)cn1] | 450 | 3.39 | D |

| Example | Structure | ESI pos + neg (Loop – Inj.) [M + H]+ | HPLC (Rt) | HPLC Method |
|---|---|---|---|---|
| 1 | 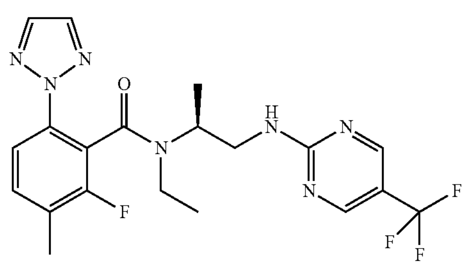 [SMILES: CCN(C(=O)c1c(-n2nccn2)ccc(C)c1F)[C@@H](C)CNc1ncc(C(F)(F)F)cn1] | 452 | 1.04 | C |

Alternative Synthesis of Example 2

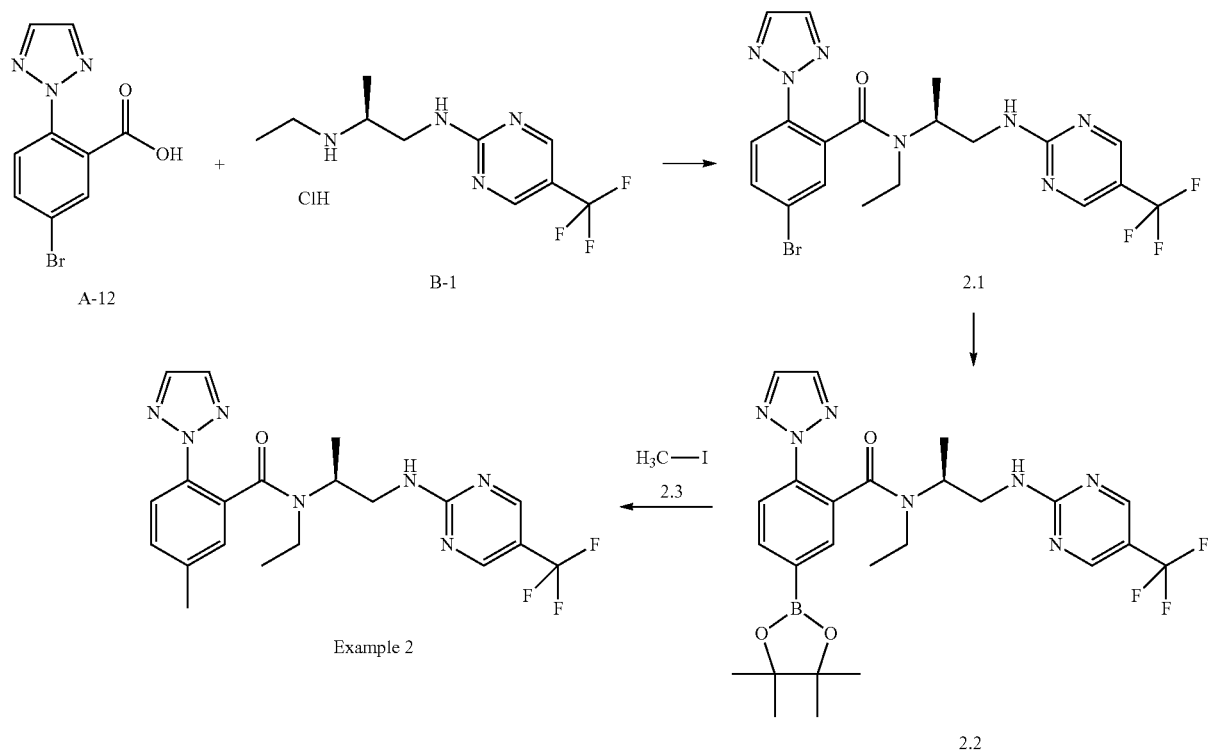

Step 1: Is carried out in analogy to the above procedure using A-12 and B-1.

Step 2: Is carried out according to WO2011/8572 A2, page 71. To a mixture of 2.1 (1.0 eq.) and KOAc (4.4 eq.) in DMSO at RT under argon is added pinacolodiboron (1.2 eq.) and Pd(dppf)Cl$_2$.DCM (0.05 eq.). The reaction flask is evacuated and purged with argon. The reaction mixture is heated at 80° C. overnight, then allowed to cool to room temperature and concentrated. The reaction mixture is diluted with H$_2$O and Et$_2$O and filtered through celite. The filtrate obtained is extracted with Et$_2$O and the organic layer is dried, filtered, and concentrated. The residue obtained is purified by flash column chromatography on silica gel to afford 2.2.

Step 3: Is carried out according to *Chem. Eur. J.* 2009, 15, 4165. In a dry flask Pd$_2$(dba)$_3$ (0.5 eq.), P(o-CH$_3$C$_6$H$_4$)$_3$ (2 eq.), and K$_2$CO$_3$ (2 eq.) are placed under argon. After addition of DMF, the mixture is stirred for 5 min at RT, followed by successive addition of solutions of 2.2 (1.0 eq) in DMF and CH$_3$I in DMF (0.4 M, 1.0 eq.). The resulting mixture is stirred under argon at 60° C. for 5 min, rapidly cooled (ice bath), filtered through a short column of SiO$_2$, and then eluted with Et$_2$O to afford Example 2.

In analogy, the $^{11}$C-radiolabelled analog of Example 2 is synthesized by using $^{11}$CH$_3$I instead of CH$_3$I.

Example 3

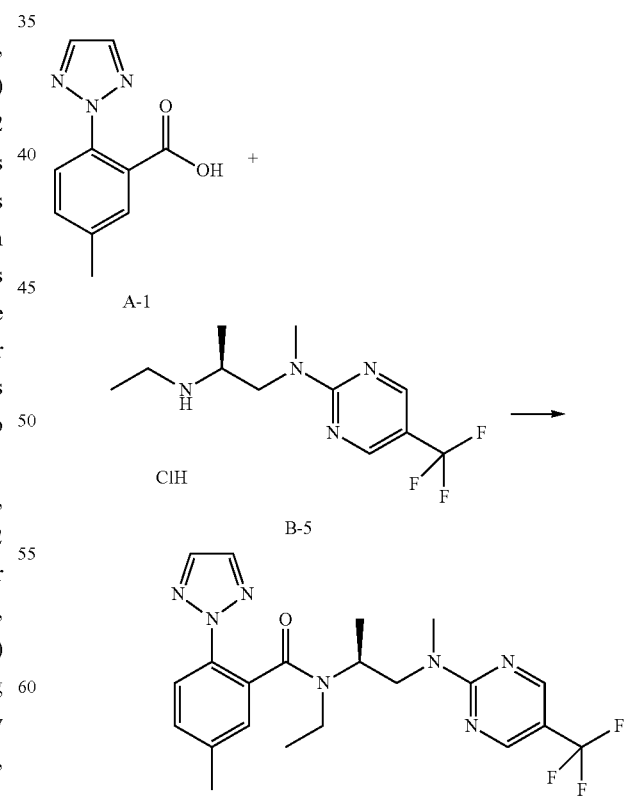

CIP (44.5 mg, 0.16 mmol) is added to a mixture of A-1 (30.0 mg, 0.15 mmol), B-5 (54.2 mg, 0.15 mmol) and DIPEA (99.0 μL, 0.58 mmol) in ACN (1.0 mL) at RT. The mixture is stirred overnight. Water (0.5 mL) and MeOH (0.5 mL) are added, the mixture is filtered and the filtrate is purified by preparative HPLC-MS (using a solvent gradient H$_2$O/ACN with NH$_4$OH) to afford 28 mg of Example 3. ESI-MS: 448 [M+Na]$^+$; HPLC (Rt): 0.78 min (method B).

The following examples are prepared in analogy to the above described procedure using the corresponding acid (see Acid Intermediates) and amine (see Amine Intermediates) as described before.

at RT for 20 min. MeI (6.00 μL, 0.10 mmol) is added and the mixture is stirred at RT for 1 h. Water is added and the mixture is directly purified by preparative HPLC-MS (using a solvent gradient H$_2$O/ACN with NH$_4$OH) to afford 33 mg of Example 3. ESI-MS: 448 [M+Na]$^+$; HPLC (Rt): 0.97 min (method E).

In analogy, Example 9 is made following the above procedure starting from Example 10.

In analogy, the $^{11}$C-radiolabelled analog of Example 3 and 9 is synthesized by using $^{11}$CH$_3$I instead of CH$_3$I.

| Example | Structure | ESI-MS [M + H]$^+$ | HPLC (Rt) [min] | HPLC Method |
|---|---|---|---|---|
| 10 | 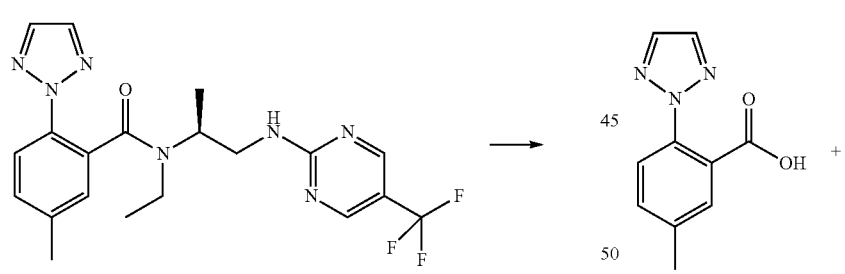 | 399 | 0.54 | B |
| 17 | 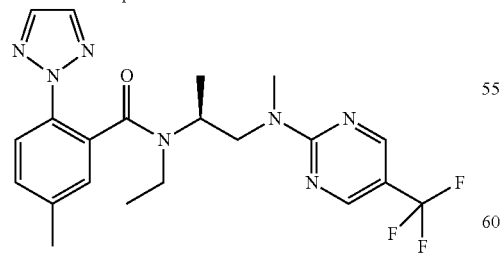 | 403 | 0.63 | E |

Alternative Synthesis for Example 3

Example 9

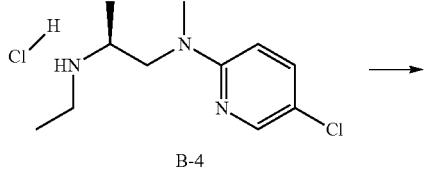

Under a nitrogen atmosphere Example 2 (35.0 mg, 0.08 mmol) is dissolved in DMF (0.75 mL). NaH (60% in mineral oil, 4.00 mg, 0.10 mmol) is added and the mixture is stirred

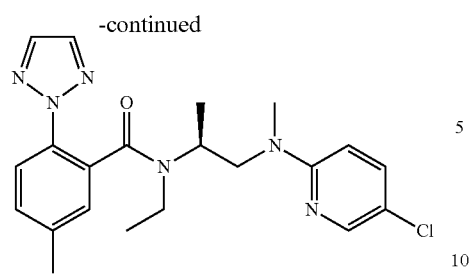

Example 9

CIP (26.0 mg, 0.09 mmol) is added to a stirred solution of A-1 (18.0 mg, 0.09 mmol), B-4 (24.6 mg, 0.08 mmol) and DIPEA (57.0 μL, 0.34 mmol) in ACN (1.0 mL) at RT. The mixture is stirred overnight. Water (0.5 mL) and MeOH (0.5 mL) are added, the mixture is filtered and the filtrate is purified by preparative LCMS (using a solvent gradient H$_2$O/ACN with NH$_4$OH) to afford 20 mg of Example 9. ESI-MS: 413 [M+Na]$^+$; HPLC (Rt): 0.65 min (method B).

Example 11

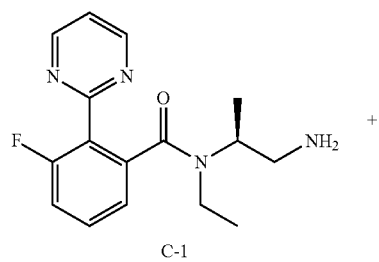

C-1

11.1

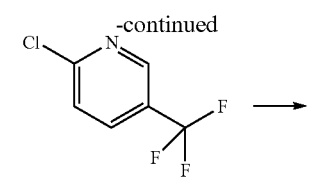

Example 11

A mixture of 11.1 (22 μL, 0.18 mmol), C-1 (46.0 mg, 0.15 mmol) and DIPEA (77 μL, 0.45 mmol) in dry DMF (1.0 mL) is heated at 70° C. overnight. The crude mixture is purified by preparative HPLC-MS (using a solvent gradient H$_2$O/ACN with NH$_4$COOH) to afford 53 mg of Example 11. ESI-MS: 470 [M+Na]$^+$; HPLC (Rt): 3.12 min (method D).

The following examples are prepared in analogy to the above described procedure using the corresponding amide (see Amide Intermediates) and corresponding substituted 2-chloro- or 2-fluoropyridine as described before, with following adjustments:

Example 13: reaction time is 2 h. Purification conditions: by flash column chromatography on silica gel (using a gradient of cyclohexane/EA from 100/0 to 10/90).

Example 15: is heated to 90° C. for 30 min by microwave

Example 16 and 18: NMP instead of DMF. The reaction is heated to 100° C. for 30 min by microwave

| Example | Structure | ESI-MS [M + H]$^+$ | HPLC (Rt) [min] | HPLC Method |
|---|---|---|---|---|
| 12 | 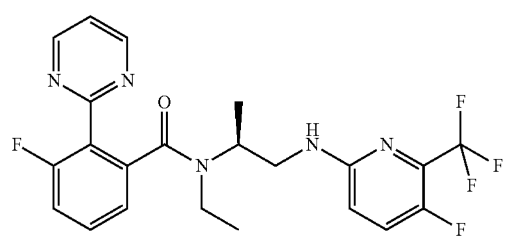 [SMILES: CCN(C(=O)c1cccc(F)c1-c1ncccn1)[C@@H](C)CNc1ccc(F)c(C(F)(F)F)n1] | [M + Na]+ 488 | 3.60 | D |
| 13 | 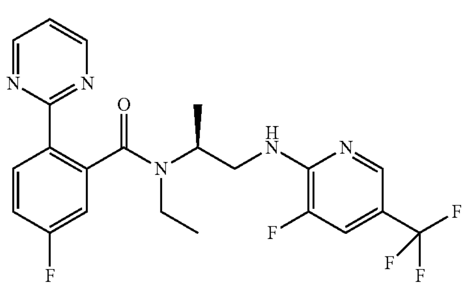 [SMILES: CCN(C(=O)c1cc(F)ccc1-c1ncccn1)[C@@H](C)CNc1ncc(C(F)(F)F)cc1F] | 466 | 4.73 | F |

-continued
| Example | Structure | ESI-MS [M + H]+ | HPLC (Rt) [min] | HPLC Method |
|---|---|---|---|---|
| 15 | 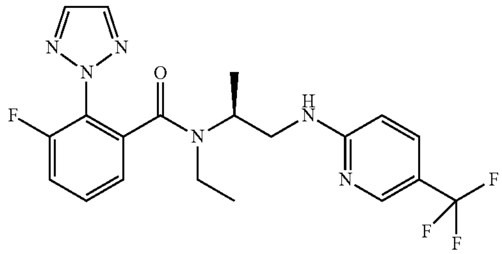 [SMILES: CCN(C(=O)c1cccc(F)c1-n1nccn1)[C@@H](C)CNc1ccc(C(F)(F)F)cn1] | 437 | 3.43 | D |
| 16 | 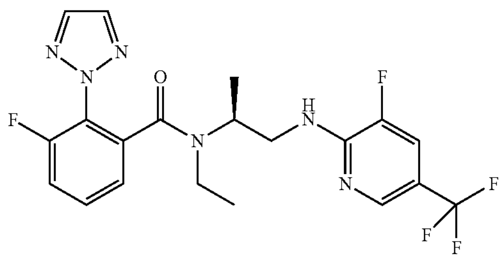 [SMILES: CCN(C(=O)c1cccc(F)c1-n1nccn1)[C@@H](C)CNc1ncc(C(F)(F)F)cc1F] | 455 | 4.90 | F |
| 18 | 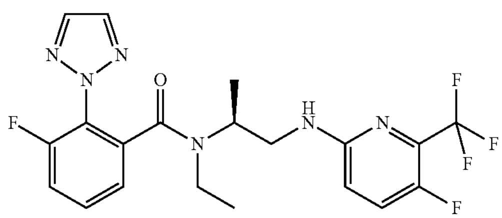 [SMILES: CCN(C(=O)c1cccc(F)c1-n1nccn1)[C@@H](C)CNc1ccc(F)c(C(F)(F)F)n1] | 455 | 3.66 | D |
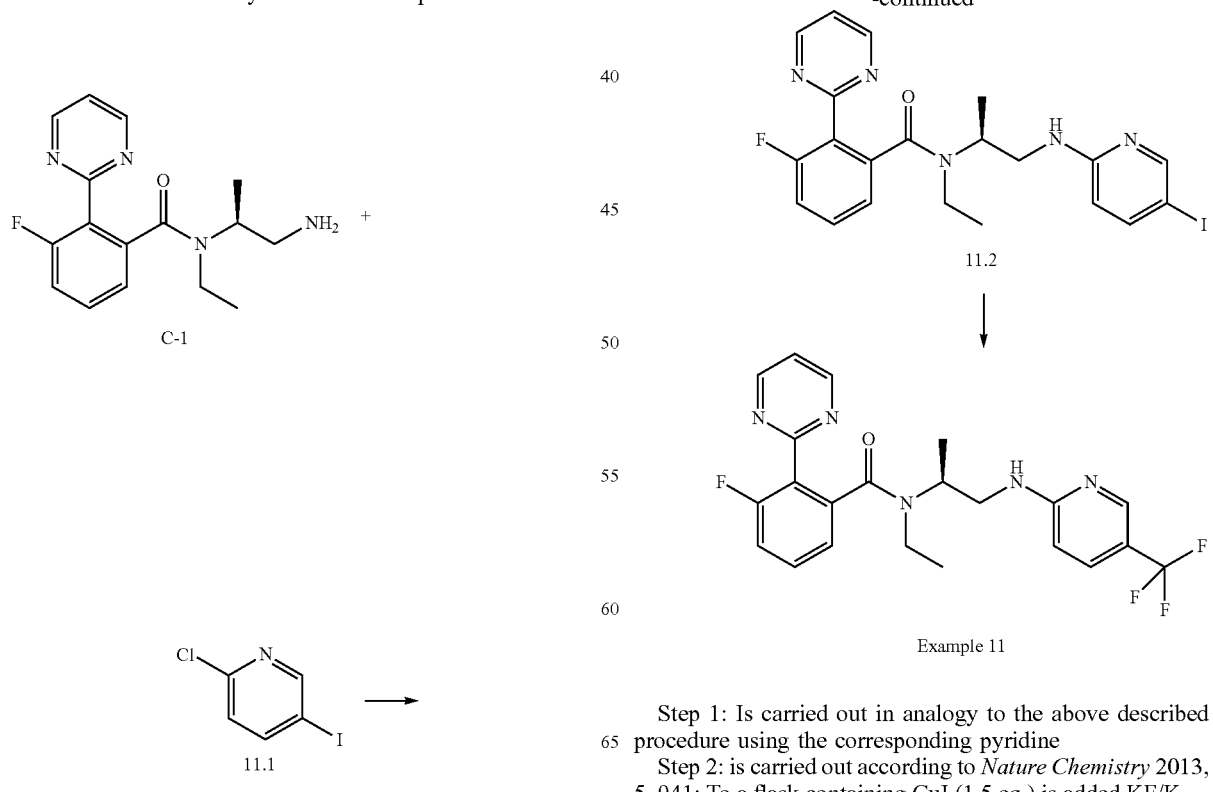
Alternative Synthesis of Example 11
Example 11
Step 1: Is carried out in analogy to the above described procedure using the corresponding pyridine
Step 2: is carried out according to *Nature Chemistry* 2013, 5, 941: To a flask containing CuI (1.5 eq.) is added $KF/K_{222}$ in ACN. The solvent was evaporated under nitrogen at 100° C. The flask s removed from heating and a solution of methyl chlorodifluoroacetate (1.5 eq.), TMEDA (1.5 eq), and 11.2 (1.5 eq.) in DMF is added via syringe. The sealed flask is heated at 150° C. for 20 min. The reaction is quenched by addition of water. Purification is performed by HPLC-MS or flash column chromatography on silica gel.

In analogy, a $^{18}$F labelled analog of Example 11 is synthesized by using [$^{18}$F]KF/K$_{222}$ instead of KF/K$_{222}$.

Other examples of the present invention containing a CF$_3$-group can be synthesized in analogy to this alternative procedure. This process is used accordingly to synthesize the $^{18}$F-radiolabelled analogs of such examples.

Example 14

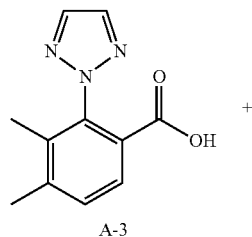

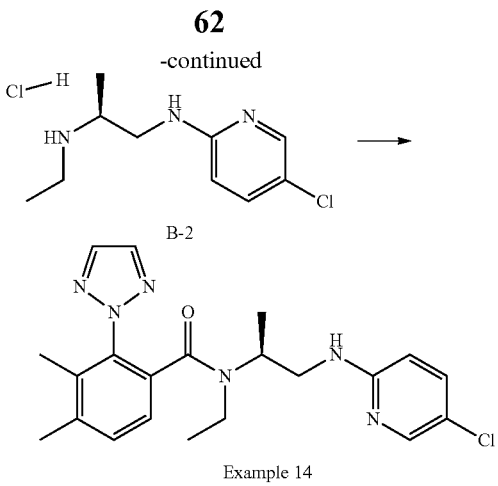

A mixture of CIP (55.0 mg, 0.20 mmol), A-3 (39.0 mg, 0.18 mmol), B-2 (39.0 mg, 0.18 mmol) and DIPEA (121 μL, 0.71 mmol) in dry ACN (1.0 mL) is stirred at RT overnight. Water (0.5 mL) and MeOH (0.5 mL) are added, the mixture is filtered and the filtrate is purified by preparative HPLC-MS (using a solvent gradient H$_2$O/ACN with NH$_4$OH) to afford 60 mg of Example 14. ES+/−: 413 [M+H]$^+$; HPLC (Rt): 0.69 min (method B).

Example 19

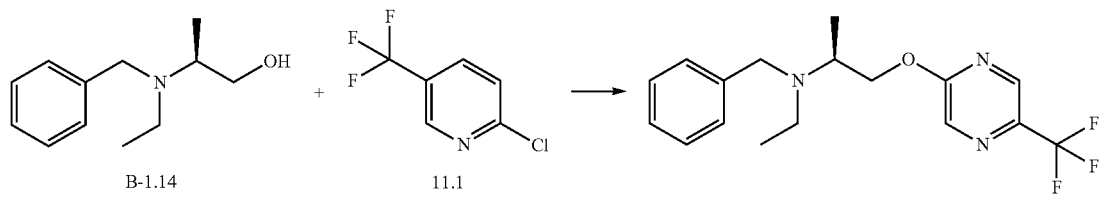

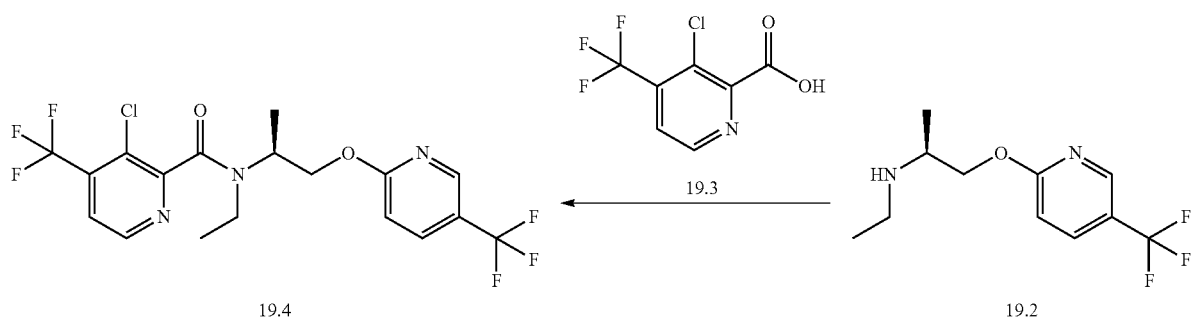

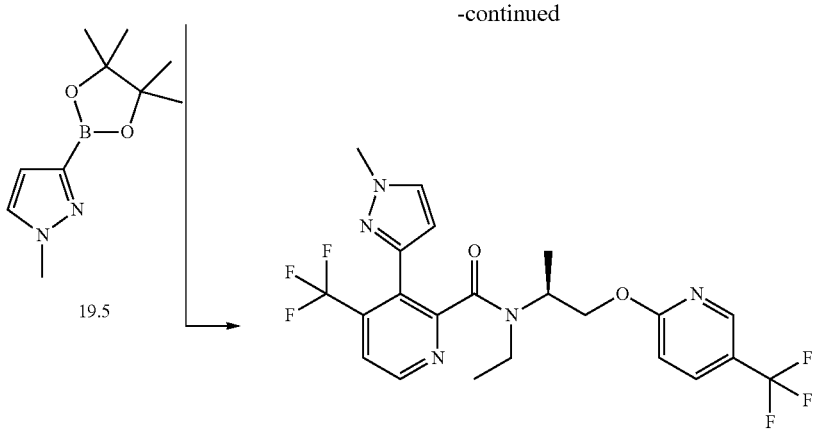

Example 19

Step 1: To a stirred solution of B-1.14 (2.75 g, 14.2 mmol) in anhydrous dioxane (80 mL) at 0° C. under nitrogen was added potassium tert-butoxide, (3.51 g, 31.1 mmol) followed by 11.1 (2.84 g, 15.6 mmol). The resulting mixture was heated to 60° C. and stirred for 2 h before being cooled to RT and quenched with water. The mixture was extracted with EtOAc and the combined organic extracts washed with brine, dried and concentrated to afford 11.3 g of 19.1 ESI-MS: 339 [M+H]+; HPLC (Rt): 1.31 min (method C).

Step 2: 19.1 (4.70 g, 12.5 mmol) is dissolved in MeOH (40 mL) and Pd/C (500 mg) is added and the mixture is stirred under an atmosphere of hydrogen (3 bar) for 3 h. The mixture is filtered through a celite pad which is washed with MeOH and the solvent is evaporated to afford 3.10 g of 19.2. ESI-MS: 249 [M+H]+; HPLC (Rt): 1.04 min (method C).

Step 3: To a mixture of 19.2 (100 mg, 0.40 mmol) and DIPEA (209 µL, 1.21 mmol) in dry ACN (3.0 mL) at RT is added CIP (146 mg, 0.52 mmol) and acid 19.3 (109 mg, 0.48 mmol) and the reaction is stirred for 2 h. Water (0.5 mL) and MeCN (0.5 mL) are added, the mixture is filtered and the filtrate is purified by preparative LCMS (using a solvent gradient H₂O/ACN with NH₄OH) to afford 120 mg of 19.4. ESI-MS: 456 [M+H]+; HPLC (Rt): 1.18 and 1.20 74 min (method C).

Step 4: To a stirred solution of 19.4 (45.6 mg, 0.10 mmol), 19.5 (41.6 mg, 0.20 mmol) and Cs₂CO₃ (97.7 mg, 0.30 mmol) in dioxane (2.0 mL) under argon was added Pd-PEPPSI-IPent catalyst (8.6 mg, 0.040 mmol) and the resulting mixture was stirred overnight at 110° C. The reaction mixture was filtered and purified by preparative HPLC (using a solvent gradient H₂O/ACN with NH₄OH) to afford 20 mg of Example 19 ESI-MS: 502 [M+H]+; HPLC (Rt): 1.13 and 1.15 min (method C).

| Example | Structure | ESI pos + neg (Loop - Inj.) [M + H]+ | HPLC (Rt) | HPLC Method |
|---|---|---|---|---|
| 19 | 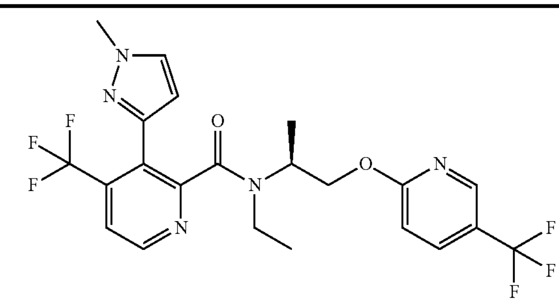 | 502 | 1.13 1.15 | C |

The invention claimed is:

1. A compound selected from the group consisting of

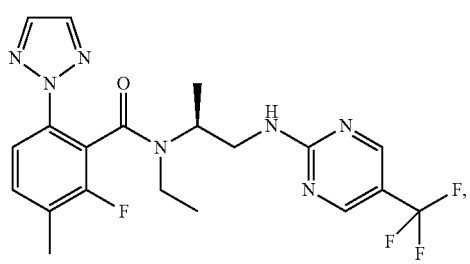

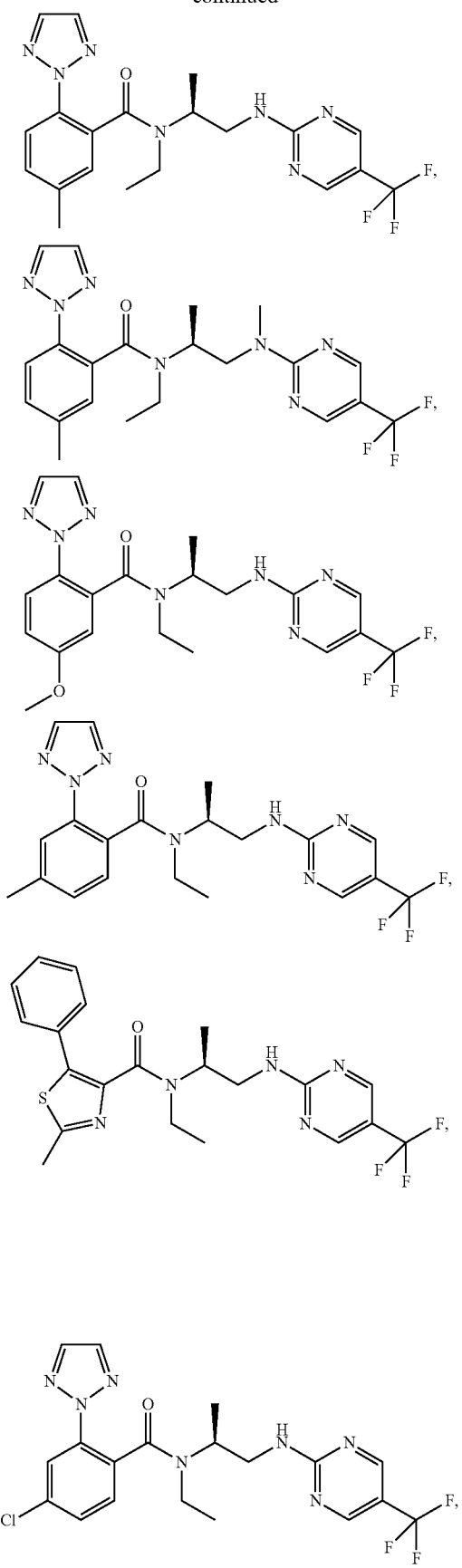
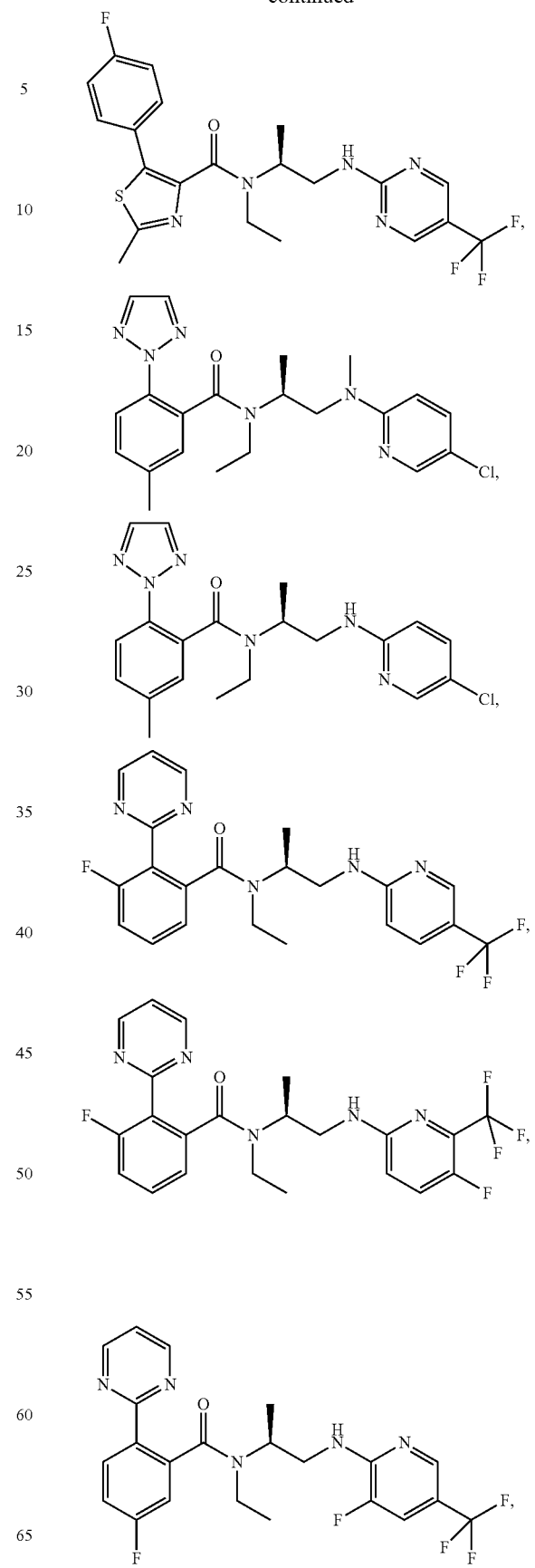

-continued

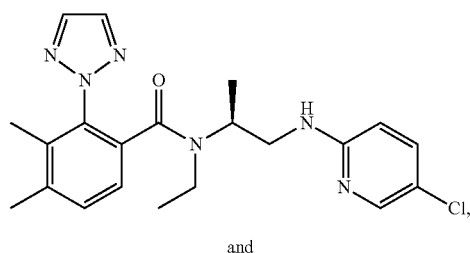

and

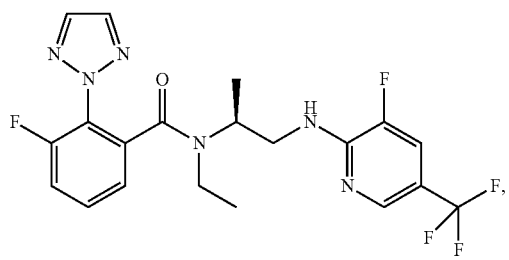

or a pharmaceutically acceptable salt thereof.

2. The compound according to claim 1 selected from the group consisting of

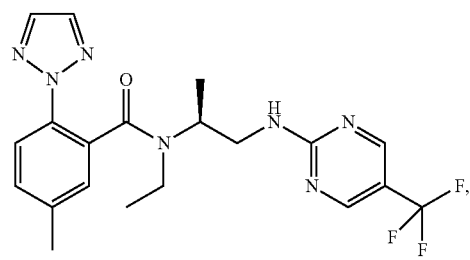

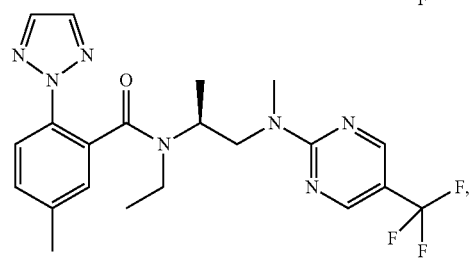

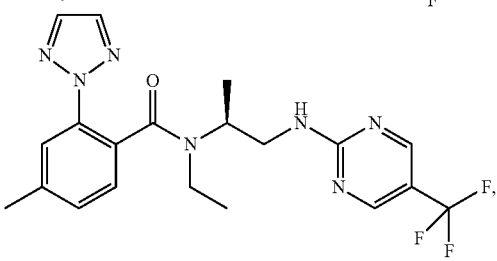

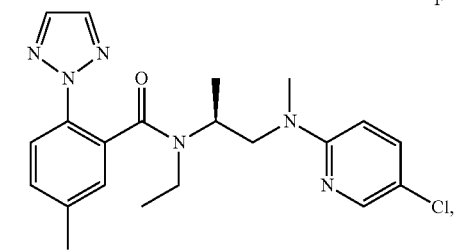

-continued

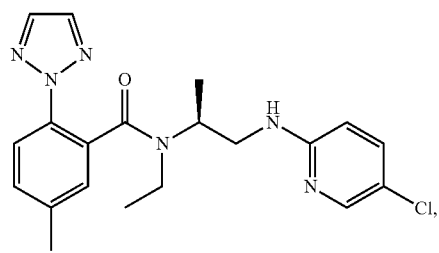

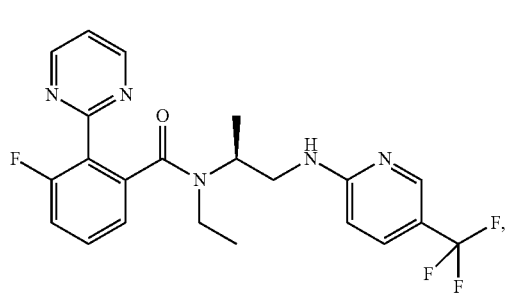

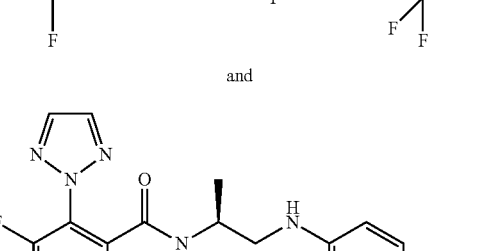

and

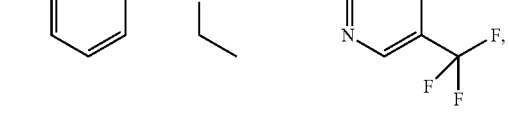

or a pharmaceutically acceptable salt thereof.

3. A pharmaceutical composition comprising a compound according to claim 1 or a pharmaceutically acceptable salt thereof in admixture with a pharmaceutically acceptable adjuvant, diluent and/or carrier.

4. A method for treating a psychiatric or neurological condition associated with impulse control deficits, the method comprising administering a compound according to claim 1 or a pharmaceutically acceptable salt thereof, to a patient in need thereof, wherein the psychiatric or neurological condition is selected from the group consisting of binge eating, bulimia, addiction, substance abuse, insomnia, and Attention Deficit Hyperactivity Disorder (ADHD.

5. A compound selected from the group consisting of
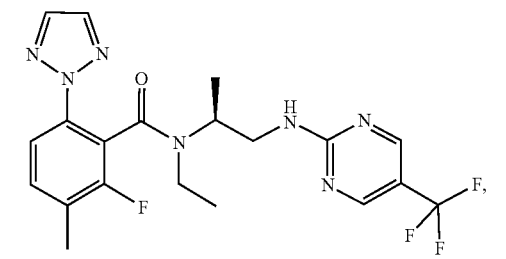
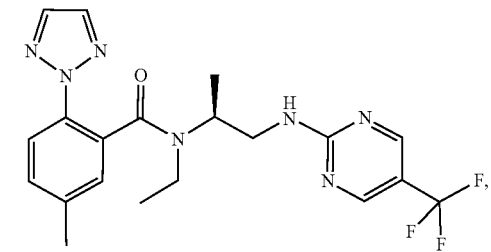
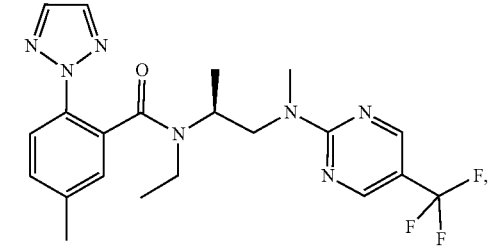
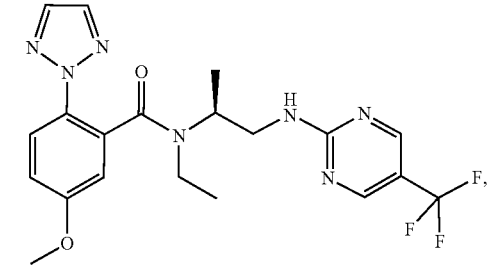
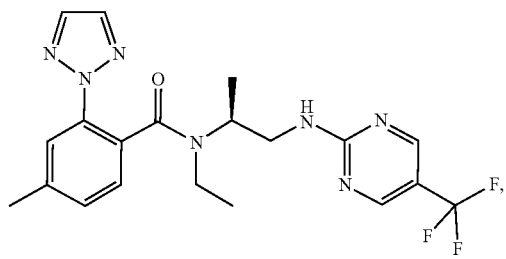
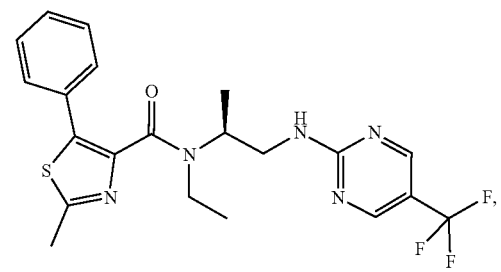
-continued
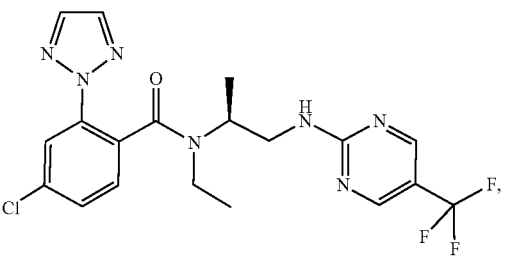
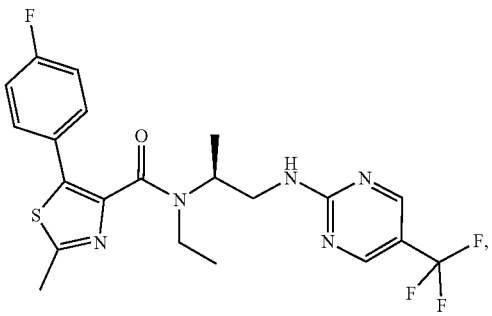
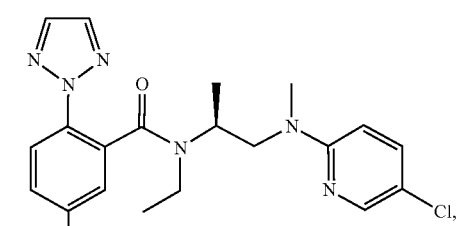
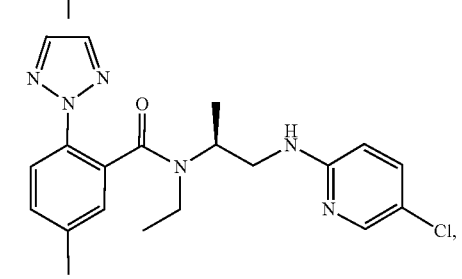
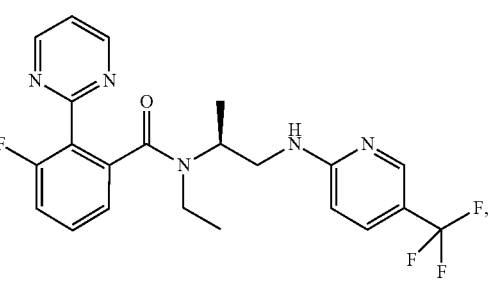
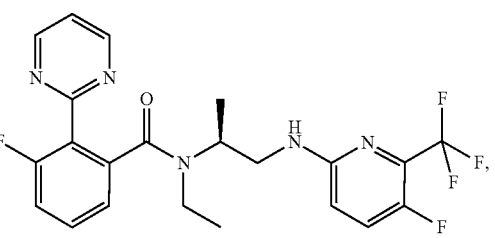

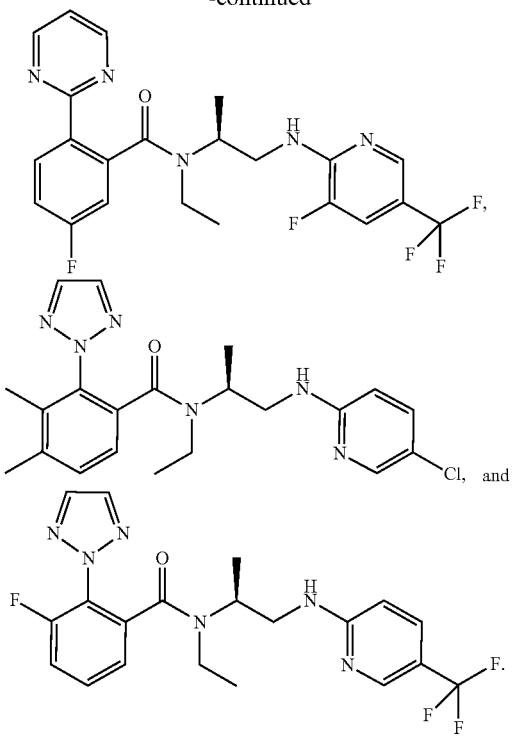

6. The compound of claim 5, selected from the group consisting of

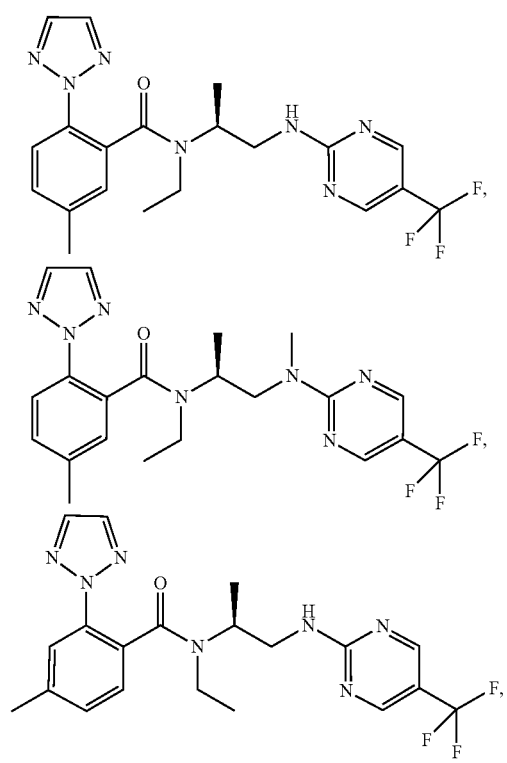

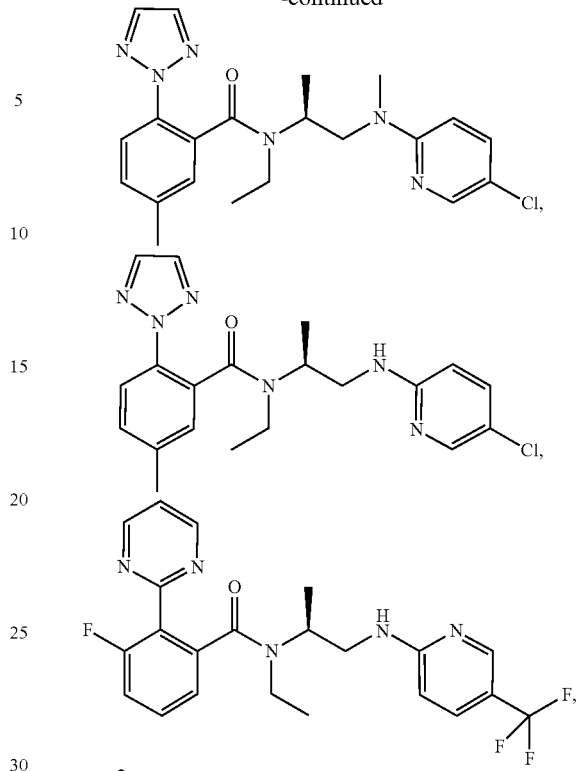

7. A pharmaceutical composition comprising a compound according to claim 5, in admixture with a pharmaceutically acceptable adjuvant, diluent and/or carrier.

8. A method for treating a psychiatric or neurological condition associated with impulse control deficits, the method comprising administering a compound according to claim 5, to a patient in need thereof, wherein the psychiatric or neurological condition is selected from the group consisting of binge eating, bulimia, addiction, substance abuse, insomnia, and Attention Deficit Hyperactivity Disorder (ADHD.

\* \* \* \* \*